US007027858B2

(12) United States Patent
Cao et al.

(10) Patent No.: US 7,027,858 B2
(45) Date of Patent: Apr. 11, 2006

(54) METHODS AND APPARATUS FOR CARDIAC R-WAVE SENSING IN A SUBCUTANEOUS ECG WAVEFORM

(75) Inventors: Jian Cao, Maplewood, MN (US); Lee B. Brian, Golden Valley, MN (US); Michael R. Kane, Higley, AZ (US); Spencer R. Hurd, Shoreview, MN (US)

(73) Assignee: Medtronic, Inc., Minneapolis, MN (US)

(*) Notice: Subject to any disclaimer, the term of this patent is extended or adjusted under 35 U.S.C. 154(b) by 637 days.

(21) Appl. No.: 10/238,140

(22) Filed: Sep. 11, 2002

(65) Prior Publication Data

US 2004/0049120 A1  Mar. 11, 2004

(51) Int. Cl.
*A61B 5/04* (2006.01)
(52) U.S. Cl. ............................... 600/521; 607/5
(58) Field of Classification Search ........ 600/515–516, 600/518, 521
See application file for complete search history.

(56) References Cited

U.S. PATENT DOCUMENTS

| | | | |
|---|---|---|---|
| 4,223,678 A | | 9/1980 | Langer et al. |
| 4,240,442 A | * | 12/1980 | Andresen et al. ........... 600/521 |
| 4,407,288 A | | 10/1983 | Langer et al. |
| 4,417,306 A | | 11/1983 | Citron et al. |
| 4,947,858 A | | 8/1990 | Smith |
| 4,974,589 A | | 12/1990 | Sholder |
| 5,117,824 A | | 6/1992 | Keimel et al. |
| 5,312,446 A | | 5/1994 | Holschbach et al. |
| 5,331,966 A | | 7/1994 | Bennett et al. |
| 5,339,820 A | | 8/1994 | Henry et al. |
| 5,381,803 A | | 1/1995 | Herleikson et al. |
| 5,658,317 A | | 8/1997 | Haefner et al. |
| 5,709,215 A | | 1/1998 | Perttu et al. |
| 5,718,242 A | | 2/1998 | McClure et al. |
| 5,738,104 A | | 4/1998 | Lo et al. |
| 5,759,196 A | | 6/1998 | Hess et al. |
| 5,785,660 A | * | 7/1998 | van Lake et al. ........... 600/523 |
| 5,851,221 A | | 12/1998 | Rieder et al. |

(Continued)

OTHER PUBLICATIONS

Draft Abstract to be submitted to XII World Congress on Cardiac Pacing and Electrophysiology (Hong Kong, Feb. 19-22, 2003).

*Primary Examiner*—Carl Layno
*Assistant Examiner*—Tammie K. Heller
(74) *Attorney, Agent, or Firm*—Paul H. McDowall; Girma Wolde-Michael

(57) ABSTRACT

The present invention uses a R-wave sensing algorithm that uniquely combines an automatic threshold adjustment method with a new noise rejection technique. This algorithm has significant advantages in avoiding the sensing of T-waves, P-waves, and noise/artifacts. Detecting the presence of noise bursts uses features that determine if an R-R interval adjacent to or within the noise signal is valid. Circuitry that discriminates noise signals from R-waves can use any one of several features including, but not limited to, the following: detection events occurring so close together that they are outside normal physiologic heart rates; frequency content that is wider than that of QRS complexes; amplitudes that are different than the adjacent or encompassing R-waves; and amplitudes that display greater than normal variability. The present invention employs multiple discrete thresholds optionally with different decay constants, alone or in combination with one or more substantially constant magnitude sensing threshold.

17 Claims, 15 Drawing Sheets

U.S. PATENT DOCUMENTS

| | | |
|---|---|---|
| 5,876,350 A | 3/1999 | Lo et al. |
| 5,957,857 A | 9/1999 | Hartley |
| 5,987,352 A | 11/1999 | Klein et al. |
| 6,230,059 B1 | 5/2001 | Duffin |
| 6,236,882 B1 | 5/2001 | Lee et al. |
| 6,438,411 B1 | 8/2002 | Guttman et al. |
| 2002/0165587 A1* | 11/2002 | Zhang et al. ............. 607/28 |
| 2003/0097077 A1* | 5/2003 | Morganroth ............ 600/509 |

* cited by examiner

METHODS AND APPARATUS FOR CARDIAC R-WAVE SENSING IN A SUBCUTANEOUS ECG WAVEFORM

FIELD OF THE INVENTION

The present invention pertains to an implantable medical devices (IMDs), such as implantable pulse generators (IGPs), implantable cardioverter-defibrillators (ICDs), insertable loop recorders (ILRs), and the like, which are adapted for sensing cardiac events and, more particularly, to such devices that provide long term monitoring of an electrocardiogram (ECG or EKG) and/or electrograms (EGMs) of a patient. More particularly, the present invention relates to configurable multi-threshold noise rejection techniques and apparatus for carrying out such techniques. The techniques of the present invention are designed to avoid sensing T-waves, P-waves, myopotential, noise and other artifact signals typically present in an ECG or EGM. Even more particularly, the present invention relates to discrimination of noisy physiologic data from relatively noise free physiologic data and selective storage or display thereof in an IMD or a graphic user interface, respectively.

BACKGROUND OF THE INVENTION

There are many instances where it is desirable to be able to diagnose intermittent spontaneous cardiac arrhythmias in ambulatory patients. Frequently faintness, syncope, and tachyarrhythmia palpitation symptoms cannot be induced and observed by the physician in tests conducted in a clinic. For many years, such patients have been equipped with external ECG monitoring systems (i.e., the patient-worn, real time Holter monitors that continuously sample the ECG from skin electrodes and record it over a certain time period). However, the ECG data must then be analyzed to locate evidence of an arrhythmia episode from which a diagnosis can be made.

As described in commonly assigned U.S. Pat. Nos. 5,312,446 and 4,947,858, the content of which are both incorporated herein by reference, externally worn ECG recorders have inherent limitations in their memory capacity for storing sampled ECG and EGM data. Cost, size, power consumption, and the sheer volume of data over time have limited real-time external Holter monitors to recording approximately 24- or 48-hour segments or recording shorter data segments associated with arrhythmias. Typically, the patient initiates storage of a data segment after the patient feels symptoms of a possible arrhythmia. The use of an externally worn Holter monitor coupled with skin electrodes is also inconvenient and uncomfortable to the patient. The skin electrodes can work loose over time with movement by the patient, and the loose electrodes generate electrical noise that is recorded along with the ECG signal and makes the subsequent analysis difficult. It has long been desired to provide an implantable monitor or recorder that is hardly noticeable by the patient and provides the capability of recording only ECG data correlated with an arrhythmia episode that is automatically detected.

The Medtronic® Reveal® ILR is intended to be implanted subcutaneously and has a pair of sense electrodes spaced apart on the device housing that are used to pick up the subcutaneous ECG which is also characterized as a "far field EGM," hereinafter to be generally referred to as "ECG" for brevity. The Reveal® ILR samples and records one or more segments (depending on the programmed operating mode) of such ECG signals. Such recordings occur only when the patient feels the effects of an arrhythmic episode and activates the recording function by holding a telemetry-based activator over the site of implantation and pressing a button. For example, the storage of a programmable length segment of the ECG can be initiated when the patient feels faint due to a bradycardia or tachycardia or feels the palpitations that accompany certain tachycardias. The memory capacity, however, is limited to a fixed number of patient- or automatically-activated events. Therefore, the segments of such ECG episode data that are stored in memory may be written over by newer ECG episode data when the auto-trigger storage and the auto-memory buffers are full. The stored segment or segments of episode data may be transmitted via an uplink telemetry transmission to an external programmer when the physician or medical care provider using the programmer initiates a memory interrogation telemetry session. Aspects of the Reveal® ILR are disclosed in commonly assigned PCT publication WO98/02209, incorporated herein by reference in its totality.

Monitoring long-term ECGs can help detect intermittent heart irregularities and syncopal events, among others. For example, U.S. Pat. No. 4,223,678, issued to Langer et al., discloses an arrhythmia record/playback component within an implantable defibrillator. ECG data is converted from analog to digital (A/D) form and stored in a first-in, first-out memory. When the defibrillator detects an arrhythmia event, it disables access to the memory so that no further ECG data is recorded in the memory until a command is received from an external monitoring device. This command requests the implantable defibrillator to transmit the stored ECG data to the monitoring device via telemetry. Langer et al., in U.S. Pat. No. 4,407,288, discloses a programmable, microprocessor-based implantable defibrillator that senses and loads ECG data into memory via a direct memory access operation. A processor analyzes this ECG data in the memory to detect the occurrence of an arrhythmia event. Upon detecting such an event, the defibrillator may initiate a therapy to terminate the arrhythmia and store the ECG data sequence of the event for transmission to an external monitoring device and later study. In normal circumstances, when no arrhythmia event is occurring, the defibrillator continuously overwrites the ECG data in the memory.

"Blanking" and "refractory" periods are commonly used in pacemakers and ICDs today. A blanking period is used to completely "mask" the presence of cardiac depolarizations, pacing output pulses, and ringing of the sense amplifiers. Refractory periods, on the other hand, allow the sense amplifier to detect the presence of intrinsic cardiac depolarizations and react to them, depending on whether they are atrial or ventricular. Until recently, however, their application in implantable monitoring devices that do not deliver therapy, and to ECG storage devices that automatically trigger their use in far field ECG recording has not been seen. Such blanking and refractory periods tend to eliminate or limit the sensing abilities of the implanted medical devices in which they are used. Examples of the use of such periods in therapy delivery device art include U.S. Pat. No. 5,759,196, issued to Hess, et al., U.S. Pat. No. 5,117,824, issued to Keimel et al., and U.S. Pat. No. 4,974,589, issued to Sholder. All these patents are incorporated by reference herein in their entireties. Nevertheless, none of these devices use such periods to exclude signals from the ECG. Although the terms "blanking" and "refractory" are normally used in devices that deliver therapies, their use may be extended to ILRs, since these periods have essentially the same function with regard to sensed events, which are the subject of the present invention.

Appropriate handling of noise and non-physiologic signal artifacts have always been an issue in ICDs. Various measures have been applied, though most involve the use of an automatically adjusting sensing threshold. In U.S. Pat. No. 5,381,803, Herleikson et al. disclose a method to arrive at a noise threshold which they claim allows the ICD to distinguish between R-waves and noise. A similar method is disclosed in U.S. Pat. No. 5,957,857 issued to Hartley et al. In U.S. Pat. No. 5,339,820 issued to Henry et al. a method is disclosed for changing the device's sensitivity threshold in response to the amplitude of a detected R-wave. In U.S. Pat. No. 5,658,317 to Haefner et al. a digital template is proposed for generating circuitry to help differentiate between native R-waves and repolarization waves (i.e., T-waves). Upon sensing a native event, the sensing threshold rises to a peak value and, from that point decreases in discrete steps by a defined percentage until the threshold achieves a low threshold value. A somewhat similar method is disclosed in U.S. Pat. No. 5,709,215, issued to Perttu et al. In U.S. Pat. No. 5,718,242 to McClure et al. a method is disclosed whereby the ICD uses the electrogram signal to distinguish between R-waves and noise. The ECG signal is converted into a plurality of discrete digital signals that are applied to both a cardiac event and morphology detector to control the sensitivity gain to eliminate sensing of noise.

Turning to heart monitors, Lo et al. have disclosed in U.S. Pat. Nos. 5,738,104 and 5,876,350 filtering methods to detect cardiac signals. In the '104 patent, they disclose the use of digital filtering to remove noise, followed by digital enhancement of the signal. In this way, they claim that the actual cardiac signals may be distinguished from various types of noise. The '350 patent emphasizes the use of a digital filtering mechanism to emphasize QRS complexes.

In U.S. Pat. No. 5,987,352, incorporated herein by reference in its totality, Klein et al. disclose a minimally invasive implantable cardiac monitoring device that has the capability to automatically capture arrhythmias without patient intervention. This invention also uses a fixed sensing threshold approach. Moreover, the device communicates its results via telemetry. More complex implantable monitors and pacemakers of this type, with more electrodes arranged in a planar array on the device housing, are disclosed in commonly assigned U.S. Pat. No. 5,331,966, incorporated herein by reference in its totality. This patent discloses the use of a subcutaneous multi-electrode system to detect and record ECGs. While the spacing of the electrodes may be critical, the ability to switch vectors enables the device to better discriminate between R-waves and noise. Three electrodes are employed to provide a pair of orthogonally sensed ECG signals at the subcutaneous implantation site. A medical electrical lead can be employed in a disclosed pacemaker embodiment to use a bipolar electrode pair in a heart chamber to provide an additional near field EGM sense signal. The P-wave or R-wave, depending on the location of the bipolar electrode pair, can then be sensed. Recording of the near field and ECG episode data can be invoked automatically by detection and satisfaction of bradycardia, tachyarrhythmia, or asystole detection criteria. Recording can also be manually commenced by the patient using an external limited function programmer or by the physician using a full function programmer.

In all of these implantable monitoring devices which possess a cardiac monitoring function, the cardiac ECG is continually sensed and sampled and the recording of ECG episode data is triggered in a variety of ways. Recordings of ECG episode data triggered by the patient using the relatively simple Reveal® ILR have proven to be of great value in diagnosing the causes of symptoms felt by the patients. Such devices also help when prescribing the implantation and programming of more complex therapy delivery IMDs, e.g., multi-programmable physiologic DDDR pacemakers and single and dual chamber ICDs.

However, many times patients are either unaware of symptom free (or essentially "silent") cardiac arrhythmias, are asleep or otherwise fail to activate the recording function (e.g., following recovery from syncope) when a bradyarrhythmia and/or a tachyarrhythmia has occurred. Thus, the accompanying ECG episode data is not recorded. It is highly desirable that such devices automatically detect an arrhythmia and initiate recording of the ECG data without having to rely upon the patient as disclosed in the above-incorporated U.S. Pat. No. 5,331,966 patent. In addition, the subcutaneous location and environment of the sensing electrode pair or pairs (typically disposed on the device housing) is relatively noisy due to myopotential signals generated by adjacent muscle groups, especially during patient exercise. Limb and trunk movements or even breathing can generate noise spikes that are superimposed upon the EGM signal and can make it appear to reflect a higher heart rate than is actually present. The myopotential noise level is not as pronounced in relation to the ECG signal level when bipolar sense electrode pairs, typically located in or close to the atrium and/or ventricle, are employed as is typically the case with bipolar implantable pacemakers and ICDs. Consequently, it is usually possible to filter out such noise in the sense amplifiers of such IMDs. And, a patient implanted with a Reveal® ILR can be instructed to assume a quiet body state when he/she initiates recording. Moreover, even if noise artifacts are recorded, they may be recorded within ECG episode data that does represent an arrhythmia felt by the patient.

In this context, if an ILR of this type is implemented with an automatic arrhythmia detection function, it will automatically commence the recording of the ECG episode data when noise artifacts are superimposed on the ECG signal. In effect, the detection algorithm mistakenly detects an arrhythmia. On the other hand, sometimes such noise is present during an actual arrhythmia that is correctly detected. Unfortunately, triggering the recording of such an ECG results in a noisy and, perhaps, useless recording. Due to the limited memory capacity, the ECG data episode that is corrupted by noise signals will replace earlier recorded ECG episode data. Earlier recordings may be relatively noise free and actually represent an arrhythmia episode of interest. The physician may find that the noisy ECG data displayed by the programmer is simply too corrupted and of no value in diagnosing the patient's cardiac condition. To counteract such a problem, the physician may have to program the ILR detection algorithm differently or turn the automatic detection and recording capability off. In such cases, the physician must rely upon the patient to trigger the recording of ECG episode data when the onset of an arrhythmia is felt.

Such issues occur most often in looping-type ECG recording systems that automatically detect arrhythmias according to specific arrhythmia detection criteria and retain segments of the ECG in recorded data memories as well as in other ECG recording systems. There are several areas in which false detection events can fill up the data storage memory of a device with essentially useless data. The phrase "false detection events," as used here, means that a predetermined number of QRS segments or R-waves has been detected over an appropriately predetermined trigger time. These set off a trigger criterion that monitors the detection of R-waves and sends the data to the trigger monitoring circuit. The trigger circuit then sets off a detect signal, forcing the implantable recorder to record a segment of the ECG into the data storage memory of the IMD.

First among likely noise sources are false detections of noise leading to false tachyarrhythmia detections; that is, inappropriate detections of an electrocardiogram segment. Muscle noise, or myopotentials, can easily dominate the ECG signal, especially when the ECG is derived from closely spaced electrodes. While it is impossible to filter out all of such noise, the circuitry is particularly susceptible to noise in the subcutaneous area where the electrodes of the small ECG implantable monitor are usually located. This noise will generally be broadband-type noise and can easily subsume the bandwidth of the standard recorded ECG. The standard recorded ECG band is a −3 dB band with ranges from 0.1 Hz to 32 Hz.

A problem caused by noise is the overreaction of the recording system such that, because of false repeat detections of the same sequence of arrhythmia, the memory overfills with segments of the same event. Such a problem is expected in an ILR ECG recording systems that automatically detects an arrhythmia and then saves data that has been monitored for a period of time previous to the detection, as well as data from a period of time following the detection. At times, this overreaction issue can be corrected by removal of noise. Then again, some of this problem can be overcome by the use of redundancy in the trigger itself. For example, a string of detected R-to-R intervals may be a condition that must be satisfied before storage of an ECG data begins.

A third noise source is electrical interference from external electrical devices in the area, commonly termed electromagnetic interference (EMI). Most common EMI is in the 60 Hz range because most alternating current and electrical devices operate in this frequency in the U.S. Any commonly available filtering techniques and digital signal processing techniques may be employed beyond what is described here for reducing this particular kind of noise.

A fourth source of false detects comes from relatively wide QRS complexes. These could include an inappropriate tachyarrhythmia detection for the occurrence of a very wide (i.e., long duration) QRS complex as are often found in patients with congestive heart failure. Such might occur if, for example, the R-wave sensing circuit had a short enough refractory period to detect multiple wavefront edges (within such a single, long duration QRS). These signals would result in multiple detections within that long QRS with the most likely number of detections being two. Thus, the R-wave detector finds several putative R-wave detections during a single QRS and, at the same time, the next QRS also has several possible R-wave detections in it. As a result, at a high enough normal rate, a very short string of such events could cause the tachyarrhythmia detection algorithm to begin recording of an episode that is not present—a false tachyarrhythmia detection.

To ensure correct discrimination between native cardiac events and such noise as described above, U.S. Pat. No. 6,236,882 issued to Lee et al., and incorporated herein by reference in its totality, discloses a looping-type memory to store cardiac events. Senses that occur within a blanking period are not detected or counted, whereas those that occur during the subsequent refractory period are not added to the trigger count that could indicate the presence of an arrhythmia. In fact, these events might cause the resetting of the trigger count. As previously discussed above in reference to U.S. Pat. Nos. 5,759,196, 5,117,824, and 4,974,589, the inventors of this patent have elected to use "blanking" and "refractory" rather than "denial" and "accommodation" intervals as used in the '882 patent.

Duffin, in U.S. Pat. No. 6,230,059, also incorporated herein by reference in its totality, teaches a method to screen out and discriminate noise from intrinsic R-waves. The device then records the noisy and relatively noise free segments of physiologic data in separate memory registers of a limited memory for retrieval and analysis at a later time.

Although both of the above patents are able to discriminate between R-waves and noise better than previous patents, there are still ways in which such discrimination can be improved, in particular, the handling of P- and T-waves and the sudden variations of R-wave amplitudes. The present invention provides novel means for such improvements.

SUMMARY OF THE INVENTION

The present invention uses an R-wave sensing algorithm that uniquely combines an automatic threshold adjustment method with a new noise rejection technique. This algorithm has significant advantages in avoiding the sensing of T-waves, P-waves, and noise/artifacts. Detecting the presence of noise bursts uses features that determine if an R-R interval adjacent to or within the noise signal is valid. Circuitry that discriminates noise signals from R-waves can use any one of several features including, but not limited to, the following: detection events occurring so close together that they are outside normal physiologic heart rates; frequency content that is wider than that of QRS complexes; amplitudes that are different than the adjacent or encompassing R-waves; and amplitudes that display greater than normal variability.

An R-R interval is considered to be valid only if the "quality" of the interval meets a certain criterion. The quality of the interval is computed from the number and duration of the detected noise bursts as these relate to the duration of the encompassing R-R interval. The circuitry will determine the detection of an arrhythmia based only on the presence of valid R-R intervals. In this way an implantable loop recorder (ILR) equipped with the present invention will be able to significantly reduce the false detection rate of arrhythmias. This reduction in false detection of myopotentials is especially important for ILRs equipped with subcutaneous electrodes.

An R-wave sensing window longer than three seconds is usually not used for ICDs or IPGs, because an output is normally scheduled well before three seconds from a previous event. But it is very important that ILRs and other implantable cardiac monitors be able to detect an asystole longer than three seconds. Therefore, the present invention provides a multi-level threshold sensitivity adjustment method when the sensing window extends beyond three seconds. This feature is designed to optimize R-wave sensing, particularly low-amplitude R-waves, during asystole and, at the same time, maintain good sensing performance of both bradycardia and tachycardia events. Significant variations in R-wave amplitudes have been observed in ILRs. The multi-level auto sensitivity threshold adjustment method of the present invention allows setting the programmed sensitivity level low enough to sense small amplitude R-waves. At the same time, this method maintains appropriate sensing margins to avoid sensing of noise.

Additionally, the present invention can be adjusted to a "quality" indicator that rates a recorded arrhythmia according to any of a number of quality indicators. If an arrhythmia event "passes" the test, it will be recorded over and replace any arrhythmia(s) previously stored in the ILR's memory.

The "quality" of an arrhythmia is a combination of indicators such as the noise quality indicator of the R-R interval encompassing an asystole or the number of valid R-R intervals out of the total number of R-R intervals used in detecting a tachycardia sequence.

The enhancements of the present invention, as compared to previous approaches, include, among others, the following. The present invention allows an ILR to manage the special attributes of subcutaneous ECGs that are detected from closely spaced electrodes, including very large T-waves and P-waves relative to the detected R-wave. Additionally, The present invention overcomes the susceptibility to large amplitude variations as well as the susceptibility of large amplitude noise signals swamping R-waves.

BRIEF DESCRIPTION OF THE DRAWINGS

The following drawings represent several embodiments of the present invention in which like elements are depicted by like reference numerals and in which the features depicted are not drawn to scale. Other embodiments and forms of the present invention will become readily apparent to those of skill in the art upon reflecting on the written disclosure in combination with the drawings. The inventors intend that all such embodiments and forms of the invention are covered hereby within the scope of patent claims issuing on this patent disclosure.

DETAILED DESCRIPTION OF THE DRAWINGS

Figure 1:
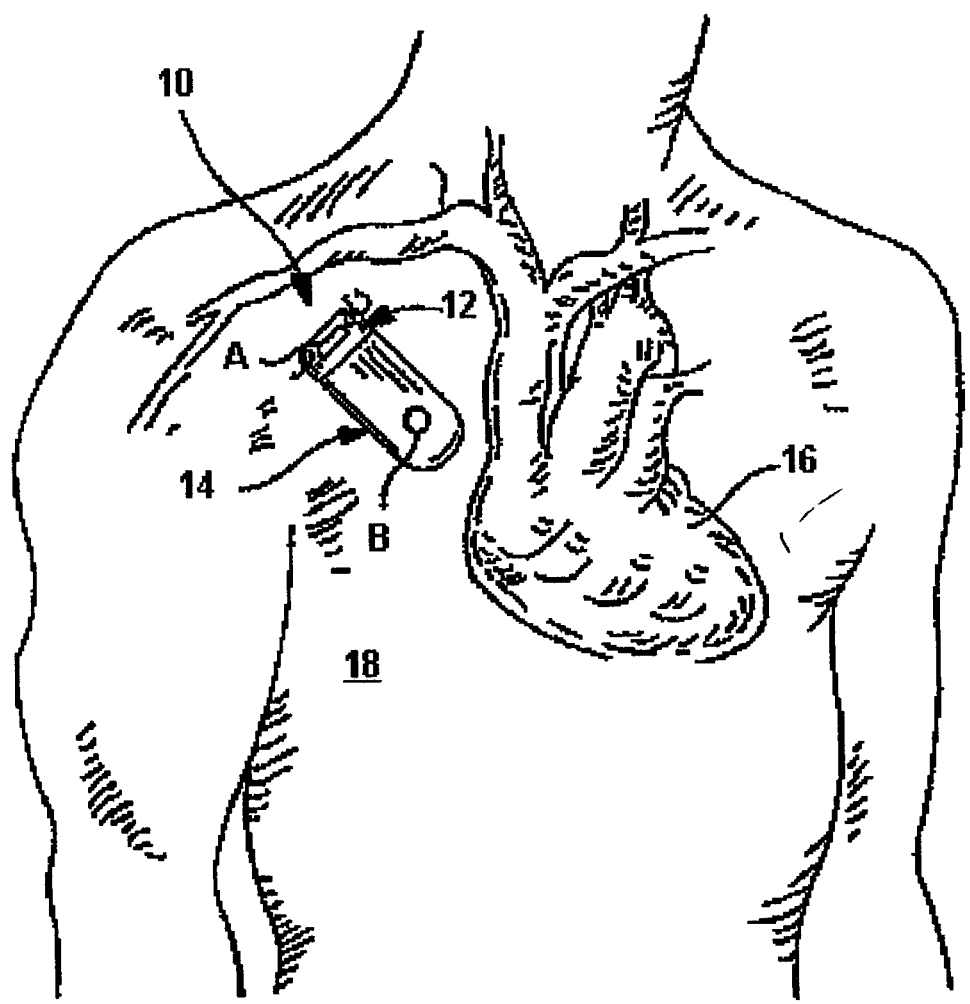
FIG. 1 is a perspective view a patient with a superimposed image of an Implantable cardiac monitor displayed as if implanted subcutaneously in the patient's body and wherein the monitor has at least one pair of subcutaneous ECG electrodes on its housing for sensing a EGM signal in which the present invention is advantageously implemented.

FIG. 1 is a simplified schematic view of implantable cardiac monitor 10 embodying the improvements of the present invention shown (superimposed) implanted subcutaneously in the upper thoracic region of a patient's body 18 and spaced from the heart 16 of the patient 18. The housing of cardiac monitor 10 may be any arbitrarily configuration, but as depicted in FIG. 1 assumes the shape of a Reveal® insertable loop recorder (ILR) manufactured by Medtronic, Inc. Note that the ILR depicted in FIG. 1 is shown enlarged in scale to the patient 18 and comprises a non-conductive header module 12 attached to hermetically sealed enclosure 14. Enclosure 14 contains the operating system of cardiac monitor 10 and is preferably conductive but may be covered in part by an electrically insulative coating. First, subcutaneous sense electrode A is formed on the surface of the header module 12 and second, subcutaneous sense electrode B is formed by an exposed portion of enclosure 14. A feedthrough extends through the mating surfaces of header module 12 and enclosure 14 to electrically connect first sense electrode A with the sensing circuitry within enclosure 14 and the conductive housing. Electrode B is directly connected with the sensing circuitry. One form of coupling header module 12 and enclosure 14 together is disclosed in commonly assigned U.S. Pat. No. 5,851,221, incorporated herein by reference.

The electrical signals attendant to the depolarization and repolarization of the heart 16 are referred to as the cardiac ECG and are sensed across sense electrodes A and B. Cardiac monitor 10 is typically sutured to subcutaneous tissue at a desired orientation of electrodes A and B to the axis of heart 16 to detect and record the ECG in a sensing vector A-B for subsequent uplink telemetry transmission to an external programmer (not shown). FIG. 1 shows only one such possible orientation of sense electrodes A and B and sense vector A-B. Because adjacent muscles of the patient (e.g., muscles in and around the chest region) generate myopotential noise signals, some orientations of electrodes A and B are preferred. However, the inventors believe that the present invention reduces, if not eliminates, the need for any particular orientating between the electrodes (and indeed of the device 10). These myopotentials can also be detected and recorded at various subcutaneous locations of sense electrodes A and B. The relative magnitudes of the ECG signal and myopotential signals can depend on their source and propagation direction with respect to a sense vector A-B between the electrodes.

In general, hermetically sealed enclosure 14 includes a lithium battery, circuitry that controls device operations and records arrhythmic ECG episode data in memory registers, and a telemetry transceiver antenna and circuit that receives downlink telemetry commands from and transmits stored data in a telemetry uplink to an external programmer. The circuitry and memory may be implemented in discrete logic or a microcomputer based system with A/D conversion of sampled ECG amplitude values. Other aspects of the Reveal® insertable loop recorder are disclosed in commonly assigned PCT publication WO98/02209.

Figure 2:
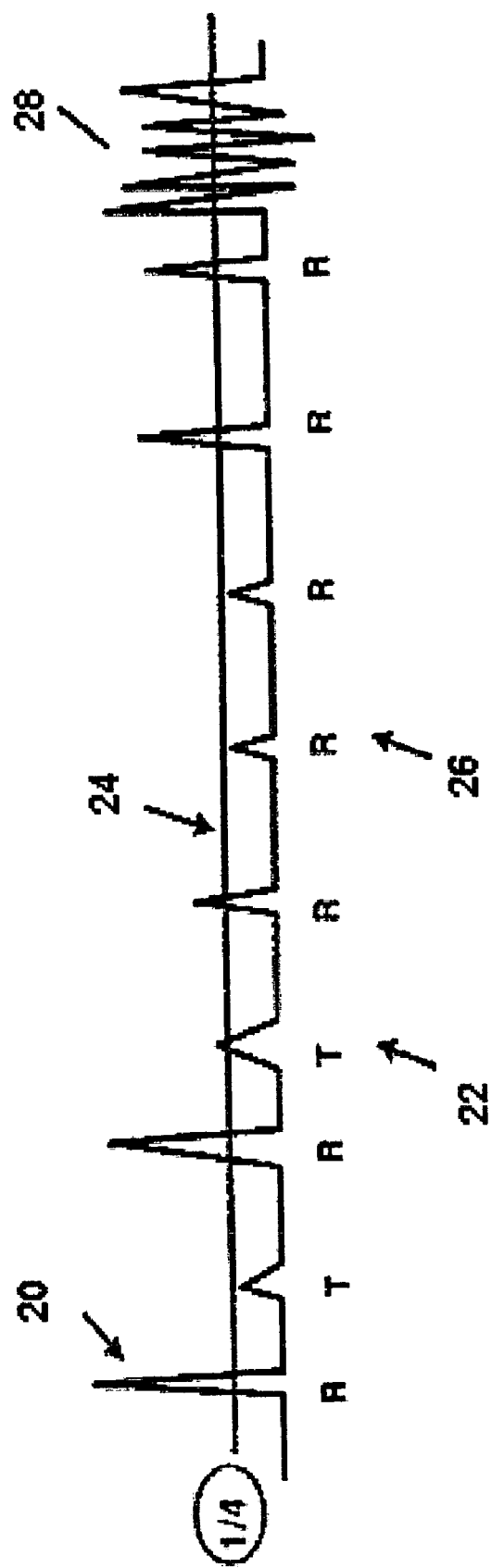
FIG. 2 depicts a prior art ECG/EGM with a fixed, programmed sensitivity threshold that cannot avoid sensing large amplitude T-waves and also fails to sense small amplitude R-waves.

FIG. 2 is an illustration of a prior art ECG/EGM display that illustrates over- and undersensing of various types of cardiac and non-cardiac signals. Programmed sensitivity 24 of the ILR may be programmed to ¼ or ½ of the maximum filtered and rectified R-wave amplitude 20. Programmed sensitivity setting 24 may result in oversensing of large T-waves 22 and/or undersensing of small R-waves 26. In addition, programmed sensitivity 24 fails to screen out electrical noise 28, such as can occur when the patient moves or exercises.

FIG. 2 illustrates the issues that can occur when using subcutaneous electrodes with one fixed programmable sensitivity threshold. There may be a significant number of oversensed events such as T-waves and noise that could lead to a false positive indication of a tachyarrhythmia (i.e., false detection event). On the other hand, due to amplitude drops in subcutaneous ECG signals during postural changes and device motions, the undersensing of small R-waves could lead the device to conclude the presence of an asystole. In either case, such events would be stored in the device's memory for further diagnosis by a physician at the next follow-up visit, or after a patient alert had been triggered. Because myopotentials can occur so readily in the presence of patient movement and/or exercise, engineers and circuit designers have attempted to ensure that ILRs can effectively screen out myopotentials and other such noise, as will become clear with reference to FIG. 3.

Figure 3:
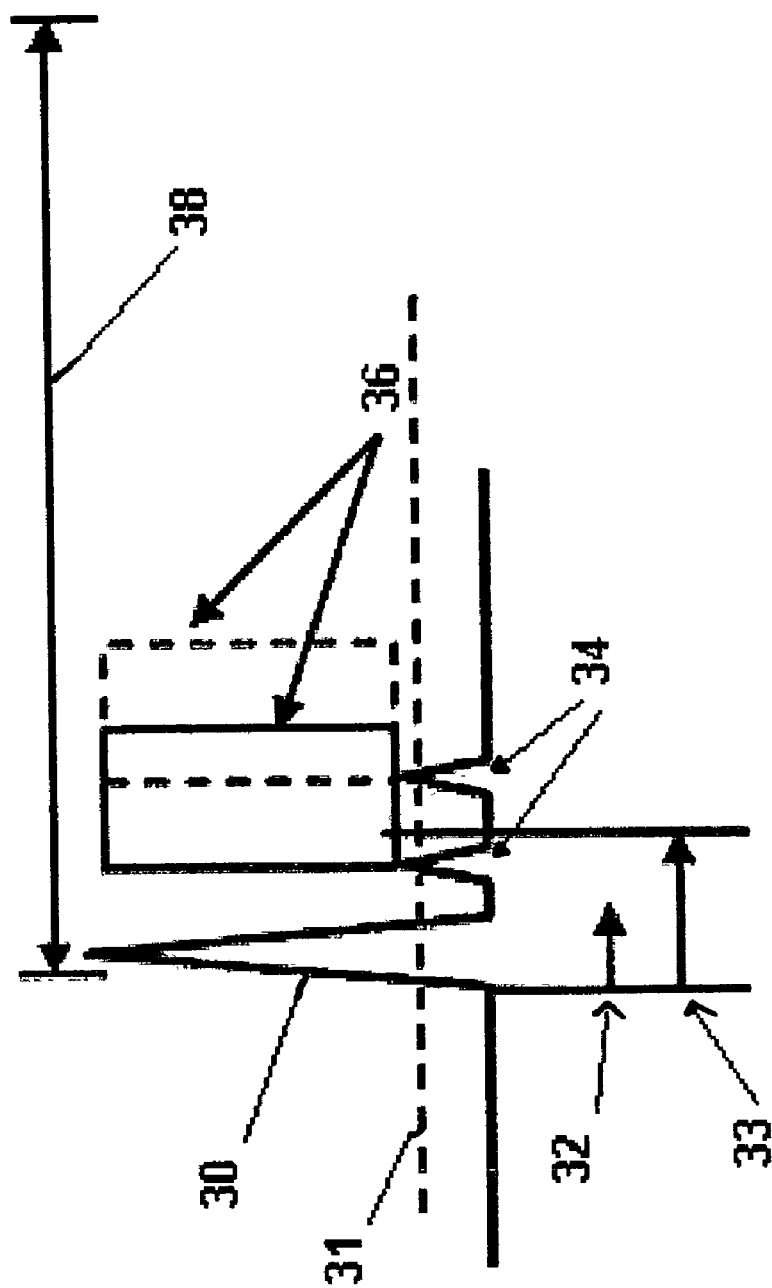
FIG. 3 illustrates a prior art embodiment of how an ILR with a fixed, programmed sensitivity threshold can screen out most noise signals using blanking and refractory periods.

FIG. 3 illustrates a prior art embodiment of how an ILR with a fixed, programmed sensitivity threshold can screen out most noise signals using blanking and refractory periods. Event 30 can be either a R-wave or the first deflection of a short, continuous noise signal. Floor level sensitivity threshold 31 has been programmed to a value chosen by the physician. In FIG. 3, the event 30 starts a simultaneous blanking period 32 and refractory period 33. Blanking period 32 may have a programmable duration (which is nominally about 65 ms), whereas refractory period 33 extends (for a nominal period of about 180 ms) after the initial sensing of event 30. Those familiar with pacing art will immediately understand the purpose of blanking period 32 and refractory period 33. Events occurring within blanking period 32 will not be sensed, whereas those events that occur outside of blanking period 32 and in refractory period(s) 33 and 36 will trigger a new refractory period. The unique nature of this extension was first introduced in the previously referenced U.S. Pat. No. 6,236,882. For the sake of simplicity, the functionality of these two periods will not be further described.

The dual events 34 could be either noise, if multiple as shown in this drawing, or, if there were only one such event, it would usually be a large amplitude T-wave. In either case, the sensing of the first of events 34 within refractory period 33 would trigger new, solid line refractory period 36. Refractory periods 36 have a nominal duration of 150 ms. If another signal 34 were sensed within solid line refractory period 36, that event would trigger a new refractory period 36 (shown by dashed line 36). In the presence of continuous noise, consecutive refractory periods would be initiated until either the noise signals stopped or until end of a timeout period 38 (nominally 1400 ms).

Initial refractory period 33 of 180 ms allows the ILR to sense intrinsic ventricular rates up to 333 bpm. Blanking period 32 of 65 ms allows the ILR to discriminate between normal, intrinsic R-waves that usually have a filtered width of less than 65 ms and "long" R-waves whose front edge may not be detected. This late detection, in other implementations, may lead to double counting or false detection of a rate that is one-half of the actual rate. A subsequent R-wave will not be sensed until the signal amplitude drops below the programmed sensitivity threshold and then rises above that threshold. Refractory periods 33 and 36 were designed to minimize sensing of noise signals, provided such signal(s) occur outside blanking period 32 and within original refractory period 33. If noise events continue to be sensed beyond 1400 ms, extended refractory periods 36 cease and all timing is reset. In such cases, the cardiac rate is determined to be normal. Note that this method of detection may not be able to effectively discriminate between the presence of noise and a high rate tachycardia episode. Due to the fixed, programmed sensitivity threshold, this method may not be robust for patients with large amplitude variations or large T/R or P/R amplitude ratios. That is, such events might be detected inappropriately.

Figure 4:
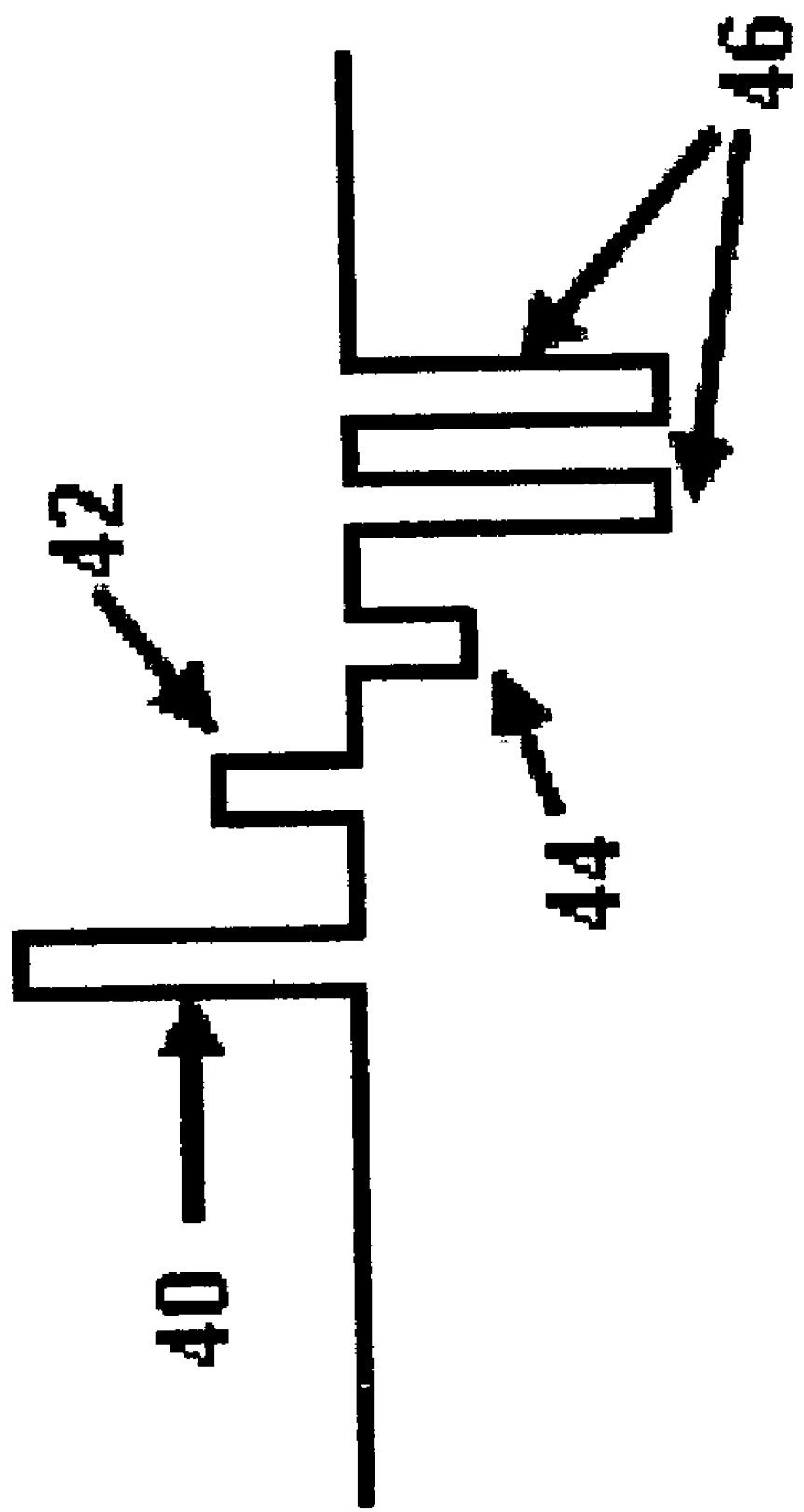
FIG. 4 is an illustration of the pertinent markers that are applicable to the present invention.

FIG. 4 depicts the marker channel® data that assist the physician in diagnosing the meaning of ECG/EGM data as it appears on the programmer printout. Sensed R-wave 40 is the datum of interest from which a physician can make a valid diagnosis. The remaining items cover data that formerly would have tended to confuse the diagnosis. Specifically, refractory-sensed event 42 takes place in the initial refractory period (see 33 in FIG. 3) after sensed R-wave 40. Refractory sensed event 42 may be a peak of a QRS complex, a noise event, or a T-wave. Event sensed in extended refractory period 44 will have been sensed in period(s) 36 as shown in FIG. 3. In most cases, sensed event 44 will be noise events, since the width of a QRS complex is usually less than the refractory period. Noise markers 46 are sensed outside of any refractory period. Because of their frequency and amplitude, noise markers 46 can be identified by the circuitry and method used in the present invention. The physician, however, may be able to use noise marker data 46 to make a clearer diagnosis.

Figure 5:
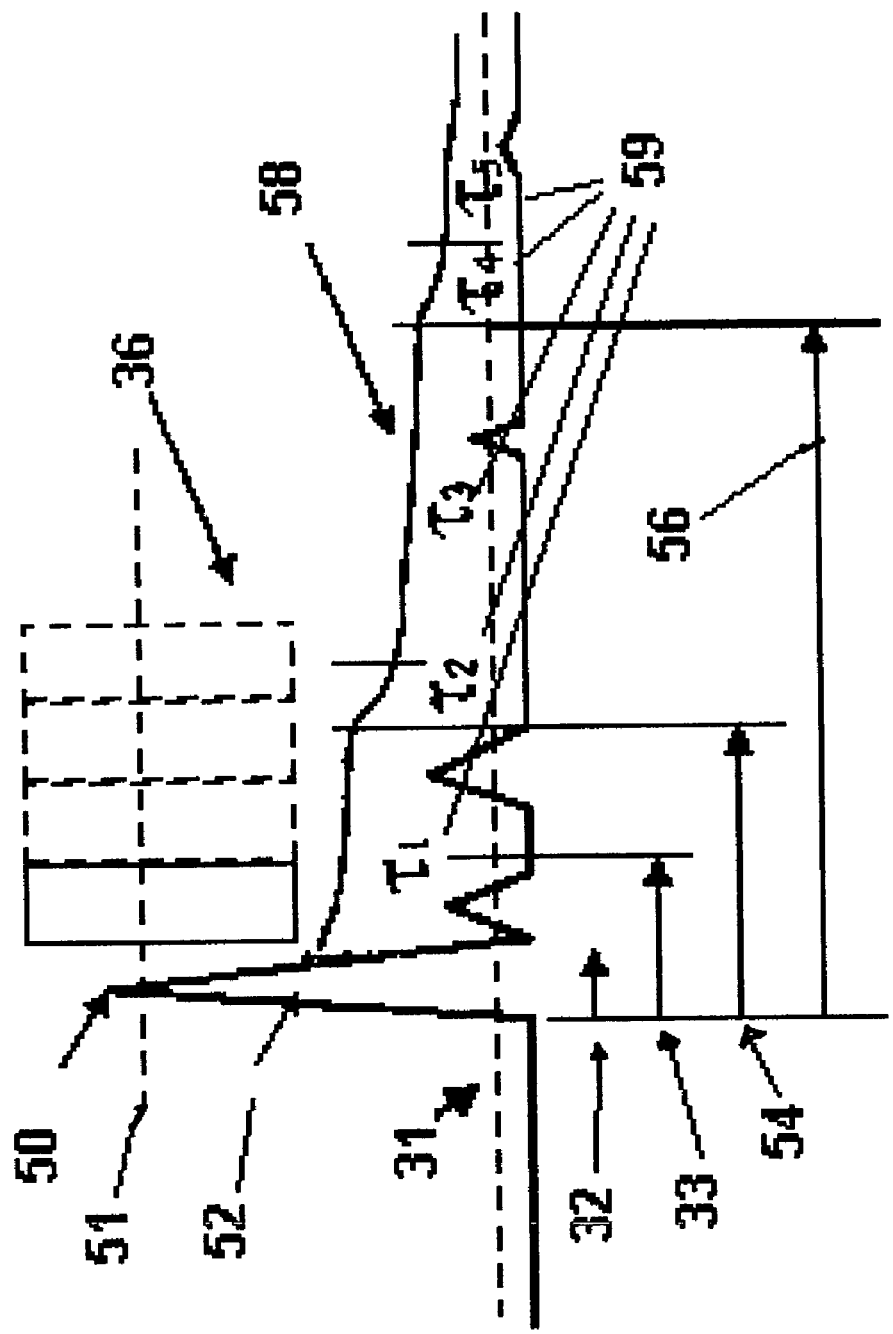
FIG. 5 depicts the preferred embodiment of the automatic threshold adjustment method designed for discriminating R-waves from other electrical signals.

FIG. 5 depicts the preferred embodiment of the automatic sensing threshold adjustment method designed for discriminating R-waves from other electrical signals. The ECG-like tracing beginning with an R-wave reaching peak value 50 illustrates a filtered and rectified ECG. Percentage of peak (A) 52 is related to the size of the sensed event's peak value 51 so as to avoid T-wave sensing and to capture relatively small R-waves during tachy episodes.

Percentage of peak ($P_{max}$) 52 will shift to a certain percentage (30–80%) of peak amplitude 50 and decay to lower programmed sensitivity threshold 58. $P_{max}$ 52 is the maximum amplitude during refractory period 33 immediately following the R-wave. $P_{max}$ 52 will not exceed upper threshold limit 51. This limit serves to avoid undersensing of smaller R-waves that follow large R-waves or noise artifacts. Upper threshold limit 51 may be user programmed or fixed as a ratio of floor level (FL) 31 (having a value from about 3× to about 20× the FL).

As depicted in FIG. 5, auto-adjusting sensitivity threshold (ST) 58 will decay exponentially to the lower threshold using the following five decay time constants 59:

$\sigma_1$=0.2 to +4 sec
$\sigma_2$=0.0 to 5.0 ($\sigma_2 \# \sigma_1$)
$\sigma_3$=0.2 to +4 sec ($\sigma_2 \# \sigma_3$)
$\sigma_4$=0.0 to 5.0 ($\sigma_4 \# \sigma_3$)
$\sigma_5$=0.0 to 5.0 ($\sigma_4 \# \sigma_5$)

ST 58 decays exponentially to FL 31 that can either be adjusted by the user or by an automatic noise tracking method. ST 58 should be programmed above the noise floor and PS should always be equal to or greater than the FL 31. Optionally, ST 58 can change to track with the noise level. The higher the noise level, the larger the ST level until it reaches the maximum defined ST level (i.e., 2× the FL).

Blanking period 32 is designed to prevent oversensing of the R-wave. Blanking period 32 may be set manually or automatically within a range of 50 to 150 ms (70 ms nominally). Blanking periods 32 should be longer than the normal filtered width of the QRS signal 50.

Refractory period 33 is designed to categorize any sensed events as other than R-waves. The period may be set manually or automatically within a range of 120 to 180 ms (130 ms nominally). The refractory period should be longer than the widest expected filtered QRS signal 50. Any event sensed within the refractory period has no effect on the currently sensed $P_{max}$ 52. Any event sensed within the refractory period, however, will automatically reset an extended refractory period 36 (of about 30 ms to about 150 ms with a nominal value of about 60 ms). Such resetting is designed to minimize the sensing of noise and other false arrhythmia events. Two methods, among others, may be used to trigger such extensions. One method extends the refractory period whenever an event is sensed within the original refractory period 33. The second method differs slightly from the first in that a refractory sensed event starts or restarts extended refractory period(s) 36. The refractory sensed event, in this method, must first drop below ST 58, with a subsequent event exceeding adjusting sensitivity threshold 58. Further details of this method may be found in the previously cited U.S. Pat. No. 6,236,882. In either method, however, a sensed event within extended refractory period(s) 36 will reset $P_{max}$ 52 to its original value, not to any new value based on the measured sensed value of the event within the extended refractory period 36.

Events sensed outside of the original refractory period 33 whose amplitudes exceed the ST 58 are considered R-waves 50. Such events reset $P_{max}$ 52.

T-wave sensing period 54 is extended manually or automatically from 200 to 500 ms with 450 ms being the nominal value. The adjusting sensitivity threshold 58 will have decayed to approximately 50% of $P_{max}$ 52 by the start of T-wave sensing period 54.

During asystole period 56 (of between about two and six seconds), with a nominal setting of three seconds, ST 58 decreases to about 25% of $P_{max}$. This level is used to avoid sensing of events with small amplitudes (i.e., P-waves or noise, during period of normal or brady arrhythmia, as well as a period of asystole). Following asystole period 56, ST decays to FL 31. ST 58 should always be greater than or equal to FL 31, with FL 31 usually programmed above the typical noise floor.

Figure 6:
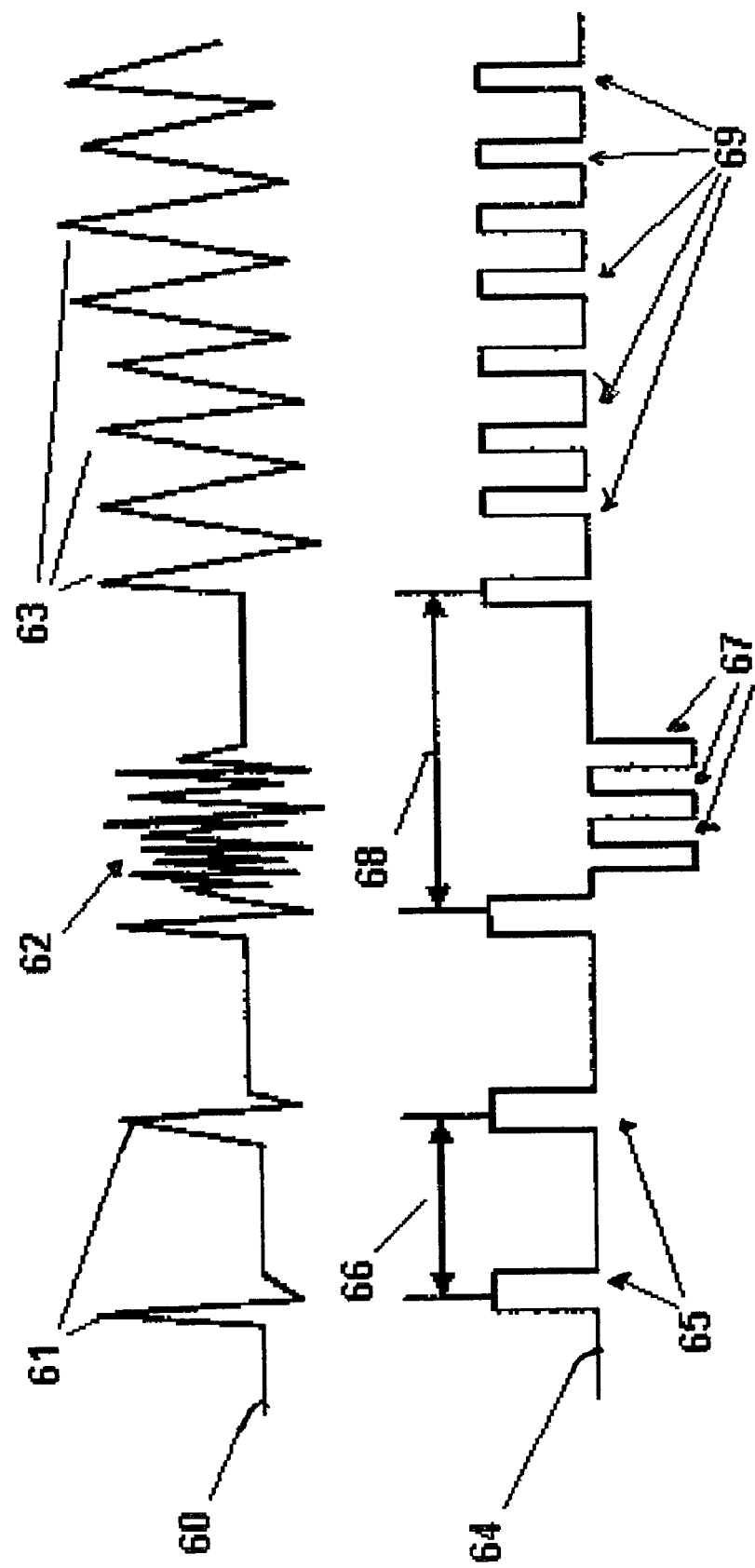
FIG. 6 illustrates valid/normal intervals as opposed to invalid/noise intervals.

FIG. 6 illustrates how the method(s) of the preferred embodiment can effectively identify, screen out, and reject noise events. On ECG 60, R-waves 61 will be marked on Marker Channel® 64 by normal R-wave sense markers 65 and interval 66 between the R-waves will be judged as a normal, valid interval. The millisecond interval between R-waves 61 is simultaneously measured. If interval 66 is greater than the tachy detect interval, nothing will be recorded.

Noise artifacts 62 on ECG 60, following an R-wave, can be part of a valid or invalid interval. In this case, the number of artifacts results in a higher number of noise markers 67 on Marker Channel 64 than the number allowed for a valid interval. Thus interval 68 is deemed to be invalid. On the other hand, if noise markers 67 are less than an allowable number, the interval may be deemed valid. In such cases, the ILR will begin recording the episode.

If, however, a tachycardia 63 starts and is recorded on ECG 60, tachy markers are recorded on Marker Channel 64. The intervals between the tachy waves are valid and, if the measured interval between the tachy waves is equal to or less than the tachy trigger interval, the episode will be recorded by the ILR.

Figure 7:
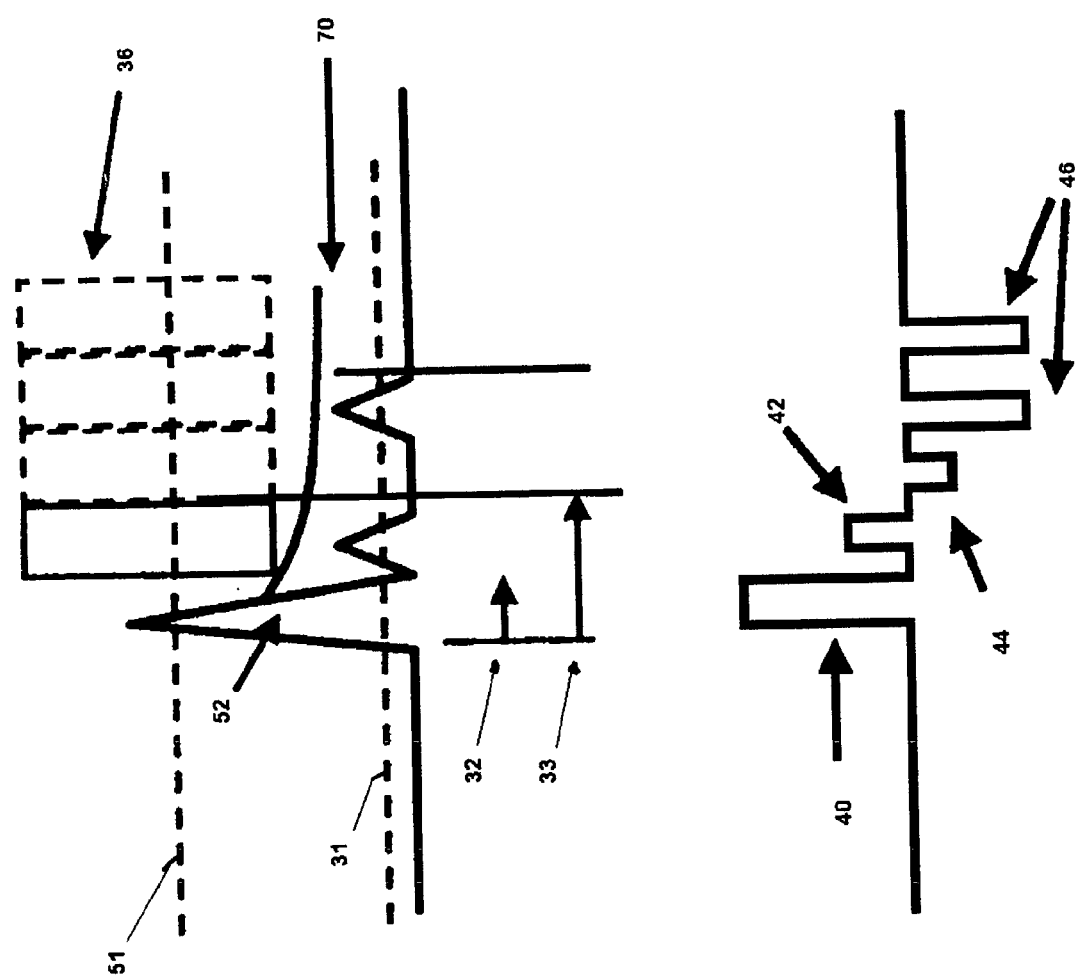
FIG. 7 is an illustration of an additional embodiment of the present invention that utilizes an R-wave sensing method with a single time constant wherein a filtered and rectified ECG appears above, and temporally aligned with an output signal produced according to the present invention.

FIG. 7 is illustrates an additional embodiment of the present invention, one in which the R-wave sensing method has a single time constant. ST 70 has a programmable decay constant of about 0.3 to 5.0 seconds. Upper threshold 51 may be adjusted from three times the FL 31 to 12 times the FL 31. All other operations and values are the same as those shown and described in FIG. 5. This single time constant embodiment involves a very simple way of sensing R-waves. Note, however, that there is no T-wave sensing interval, as appears in FIG. 5 (and as will be presented again in FIG. 8). Thus, the possibility exists that T-wave oversensing may occur in this embodiment. Those of skill in the art may not similarity between FIG. 7 and some prior art approaches to exponential decaying sensing thresholds in the cardiac pacing art. However, the embodiment depicted in FIG. 7 differs from such prior art in at least a couple respects. First, the prior art fails to disclose the type of marker data that corresponds to cardiac events according to the present invention. Second, the prior art techniques are typically interrupted by a pacing event in lieu of the continued asystole monitoring of the present invention. Third, the prior art does not practice or disclose the foregoing in addition to the sequentially extendable refractory period(s) 36. The embodiment depicted in FIG. 7 does not represent a preferred embodiment of the present invention.

Figure 8:
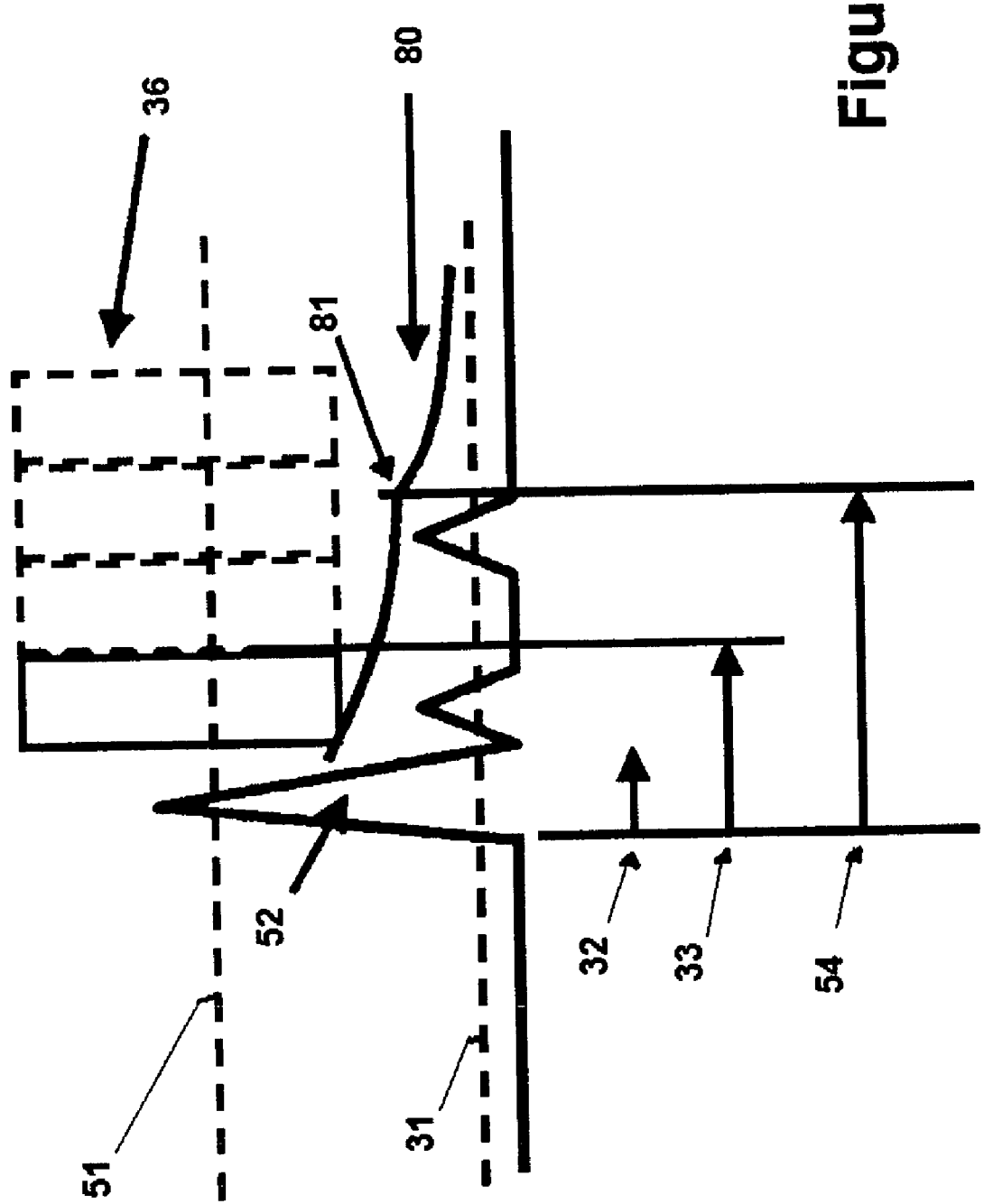
FIG. 8 depicts a further embodiment of the present invention that uses two different time constants employed in a dual decay time constant technique applied sequentially to an ECG.

FIG. 8 depicts a further additional embodiment of the present invention, one that uses a dual level auto ST adjustment method. The purpose of this dual decay time constant is to effectively avoid T-wave oversensing while maintaining good R-wave sensing. ST 80 will start at 50% of peak value 52 as compared to upper threshold 51. Note that the upper threshold limit may be as high as 9× FL 31. From peak value 52, ST 80 decays exponentially to the first time constant 81, that is, at 2.0 seconds. After T-wave temporal window 54 closes (i.e., ends), the ST 80 decays exponentially to FL 31 at a second smaller time constant, that is, 0.5 sec.

Compared to the single time constant embodiment (FIG. 7), the dual decay time constant of this embodiment can sense more R-waves, and is thus a preferred mode of the present invention. The reason that more R-waves can be sensed involves the 50% peak value 52. The algorithm is able to detect large changes in R-wave amplitude during normal sinus rhythm. On the other hand, the algorithm in this embodiment also makes it possible to detect noise artifacts (not shown) that may occur during asystole or bradycardia rhythms involving extended R-wave intervals.

Figure 9:
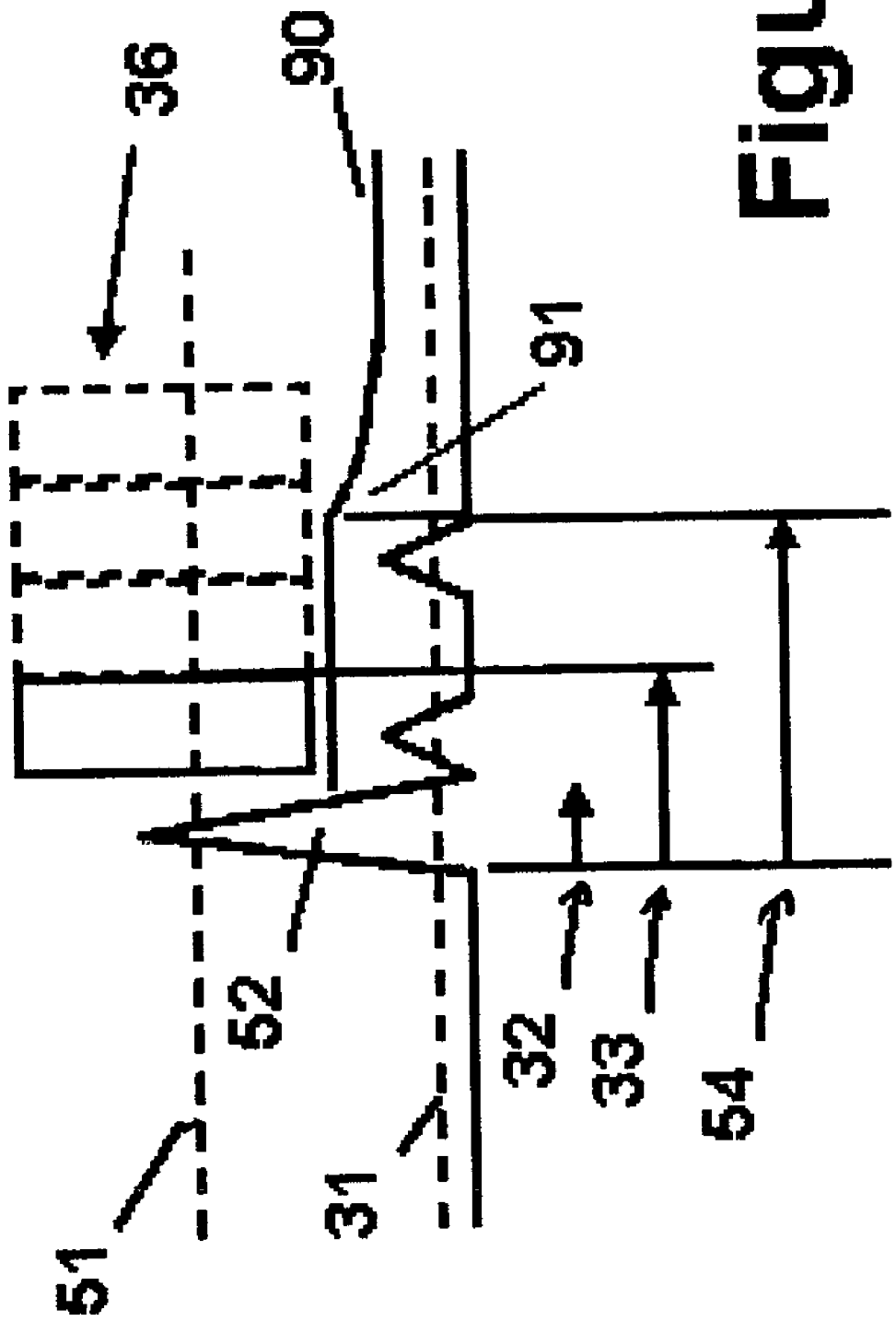
FIG. 9 depicts an additional embodiment of the present invention that as depicted employs an alternative dual level auto-sensitivity threshold adjustment technique, and wherein the first threshold has a substantially constant magnitude.

FIG. 9 depicts an additional embodiment of the present invention, one that uses an alternative dual level auto ST adjustment method. The purpose of this flat initial ST throughout T-wave window 54 is to both avoid T-wave oversensing as well as the sensing of closely coupled R-waves of lesser amplitude than the initial R-wave that triggers all the other intervals. ST 90 can begin at about 50% of peak value 52 as compared to upper threshold 51. Note that the upper threshold limit may be as high as 9×FL 31. From peak value 52, ST 80 remains flat. After T-wave window 54 closes, the ST 80 decays exponentially to FL 31 at a time constant of 2.0 sec.

Compared to the dual decay time constant embodiment (FIG. 8), the algorithm used in this embodiment can avoid sensing T-waves and larger amplitude, closely coupled R-waves. The reason for this involves the 50% peak value 52. Because the first portion of ST is flat at half of maximum threshold 52, the algorithm is unable to detect T-waves and smaller amplitude R-waves. On the other hand, and due to the decay that begins at the end of T-wave window 54, the algorithm in this embodiment also makes it possible to detect noise artifacts (not shown) that may occur during asystole or bradycardia rhythms involving extended R-wave intervals.

Figure 10:
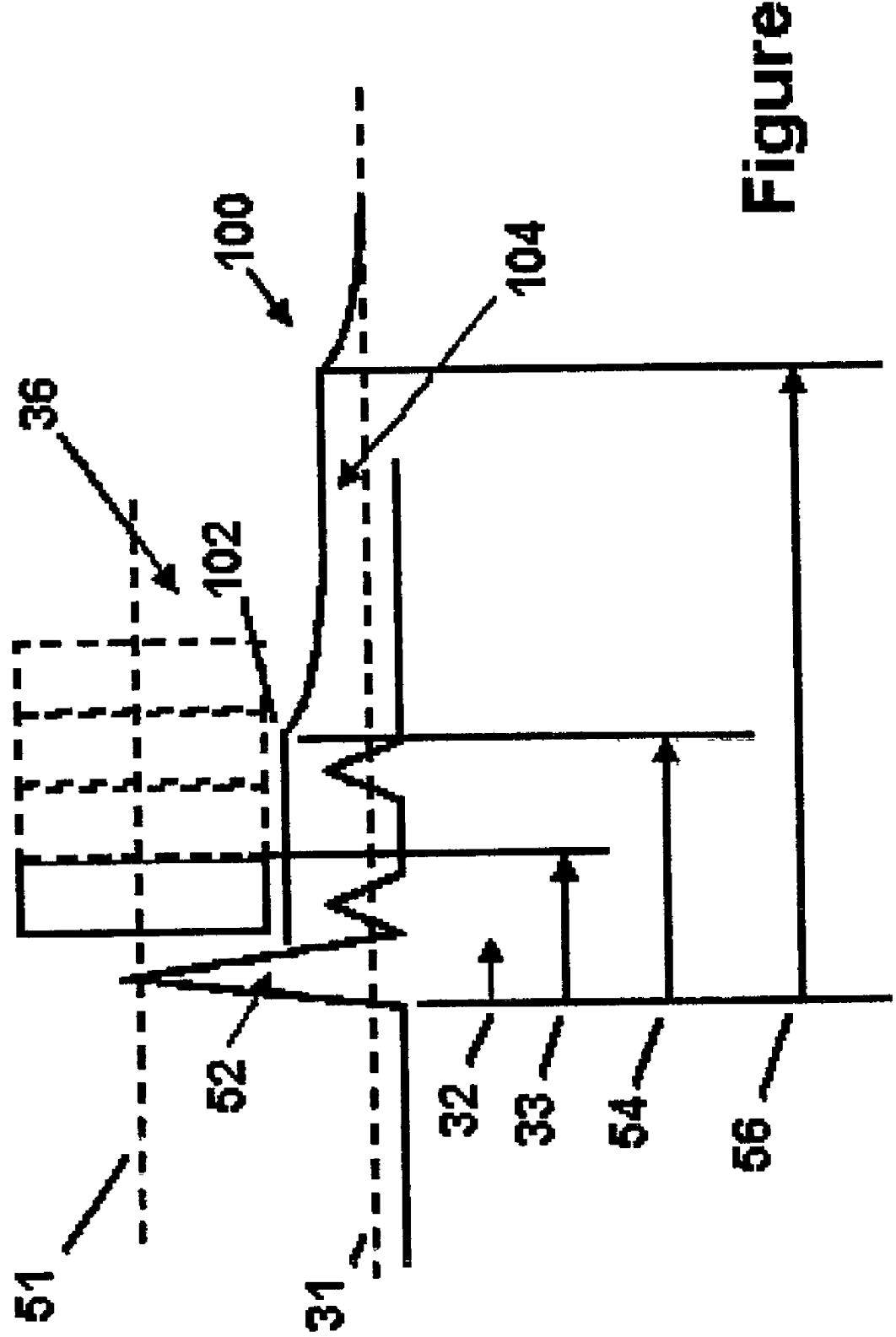
FIG. 10 is an additional embodiment of the present invention, one that uses a multi-level sensitivity threshold using different time constant decays to lower the sensitivity threshold from one level to the next.

FIG. 10 depicts an additional, and yet more preferred embodiment of the present invention, one that uses a multi-level ST adjustment method. During the initial period corresponding to T-wave window 54, ST 100 remains at 50% of peak value 52 as compared to upper threshold 51. The purpose of this flat initial ST throughout T-wave window 54 is to both avoid T-wave oversensing as well as good sensing of R-waves during a tachy episode. From peak value 52, ST 100 remains flat for about 450 ms until it reaches the start of the first time constant 102. After T-wave window 54 closes ST 104 decays slowly, using a first time constant, for a period varying between two and about six seconds, until the end of asystole window 56 ranging from 2 to 6 seconds (2 seconds nominally), where it reaches a value of about 25% of maximum threshold 52, assuming artifacts are less than 25% of upper threshold. Thereafter, ST 100 decays exponentially to Fl 31, using a second time constant. This additional decay allows the device to eliminate the sensing of P-waves.

In addition to the advantages mentioned above in FIG. 9, this R-wave sensing method allows a method for storing temporal data sequence(s) of tachycardia event(s) in other bins (not shown) than in the tachy memory bin. For example, should the tachy memory bin be filled, a tachycardia event might be stored in the asystole or brady bin, by comparing the time of the new episode to episodes already stored in these bins. Of course, a new asystole or a brady episode occurs and the bins are full, the tachy events can be overwritten by the new asystole or the brady episode. Thus the allocated storage space for asystole or brady events is not affected. Storage in these alternative bins can be based on criteria such as the most recent episode, the duration of the episode, quality of signals, and tachy rate, among others. The data storage with priority method described above will fully use the storage space of the device and arrhythmia detection performance can be further enhanced.

Figure 11:
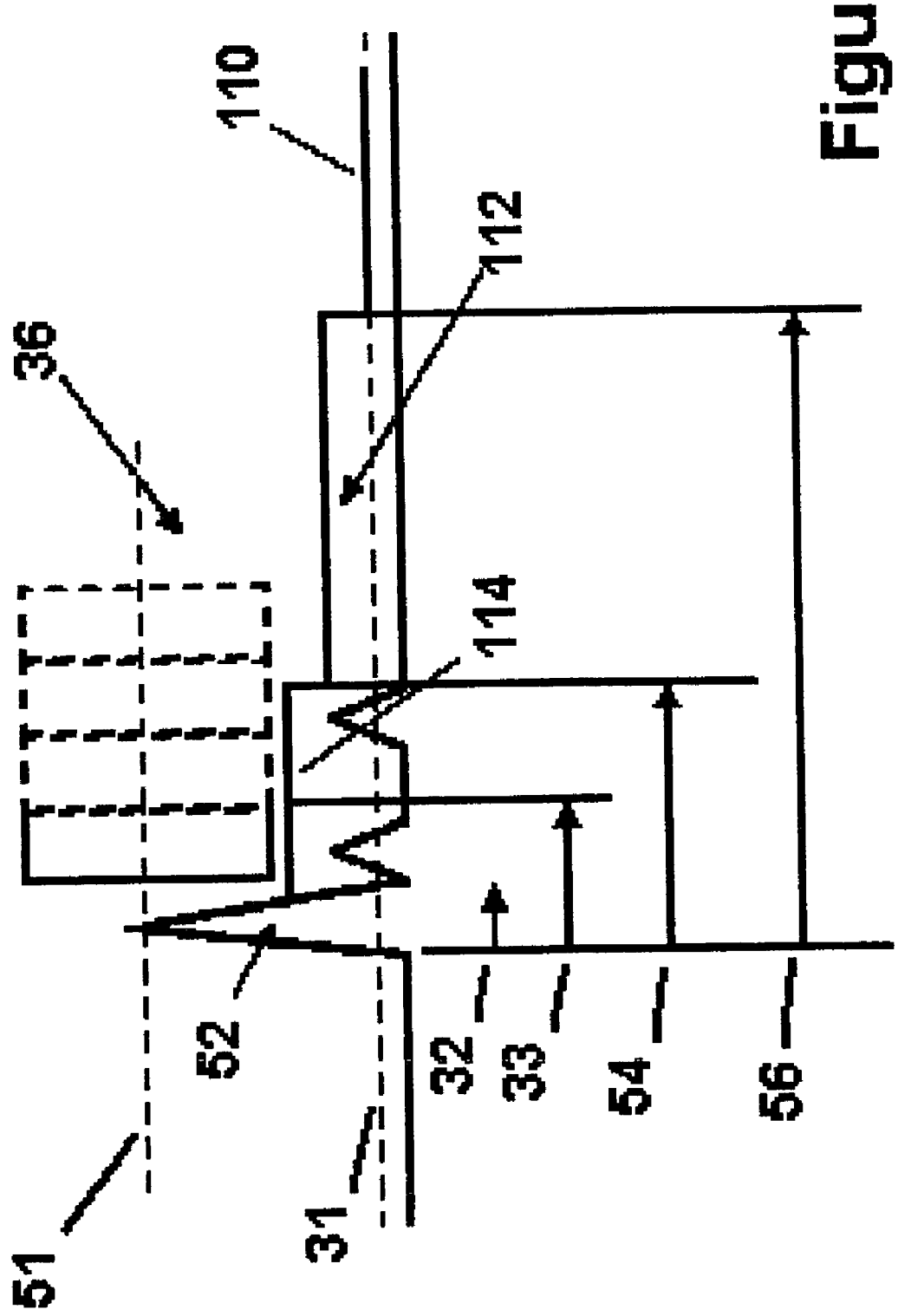
FIG. 11 is an additional embodiment of the present invention that uses discrete drops to change from one sensitivity threshold level to the next.

FIG. 11 is an additional embodiment of the present invention, one that uses discrete drops in the sensitivity threshold to change from one threshold level to the next. During the initial period corresponding to T-wave window 54, ST 114 remains at 50% of peak value 52 as compared to upper threshold 51. The purpose of this flat initial ST throughout T-wave window 54 is to both avoid T-wave oversensing as well as good sensing of R-waves during a tachy episode. From 50% peak value 52, ST 114 remains flat for about 450 ms then drops 25% to ST level 112, for a period varying between two and about six seconds, until the end of asystole window 56, where it drops again for a preset time to match FL 31 at level 110 assuming there are no sensed events to trigger a rise in FL 31. This method may be simpler especially when a digital implementation is used.

Figure 12:
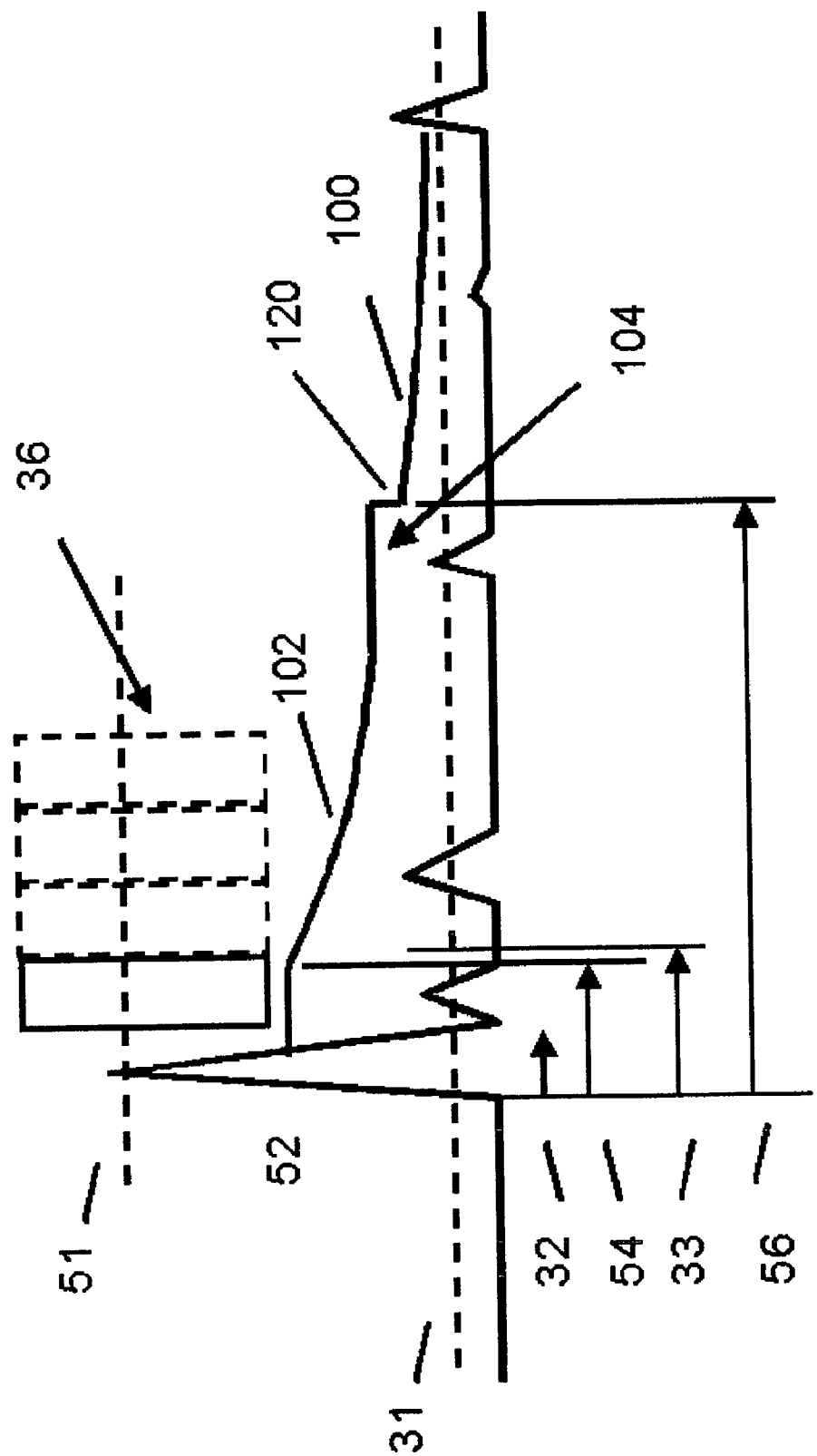
FIG. 12 is a further embodiment of the present invention, one that uses a multi-level sensitivity threshold with several fixed delay constants.

FIG. 12 is a further embodiment of the present invention. Threshold hold time 54 of 0–500 ms (100 ms nominally) can be less than refractory period 33. During threshold hold time 54, ST 102 will be fixed at 50–70% of $P_{max}$ 52. This period is designed to increase the safety margin for avoiding T-wave oversensing. Thereafter, ST 102 will decay to level 104 that is approximately 30% of $P_{max}$ 52. ST 102 must be above 30% of $P_{max}$ 52 before asystole window 56 (1.5 seconds nominally). This particular level is designed to provide an appropriate margin of safety to avoid sensing of P-waves, noise, or artifacts. This design is based on the fact that R/P amplitude ratio may not decrease significantly when the location of a P-wave is far apart from the previous R-wave. Therefore, a fixed lower limit is appropriate to avoid sensing large amplitude P-waves. At asystole window 56, ST 120 will drop to a lower level that is 20% of $P_{max}$ 52. Then, ST 100 will further decay to FL 31. The low sensitivity threshold after asystole window 56 is designed to capture R-waves with very small amplitudes while keeping a low false detection rate due to sudden R-wave amplitude changes. FL 31 should be set above the noise level and it should be ideally just below the smallest R-waves at various postures. If possible P-wave amplitudes should be selected to be smaller than FL 31.

Figure 13:
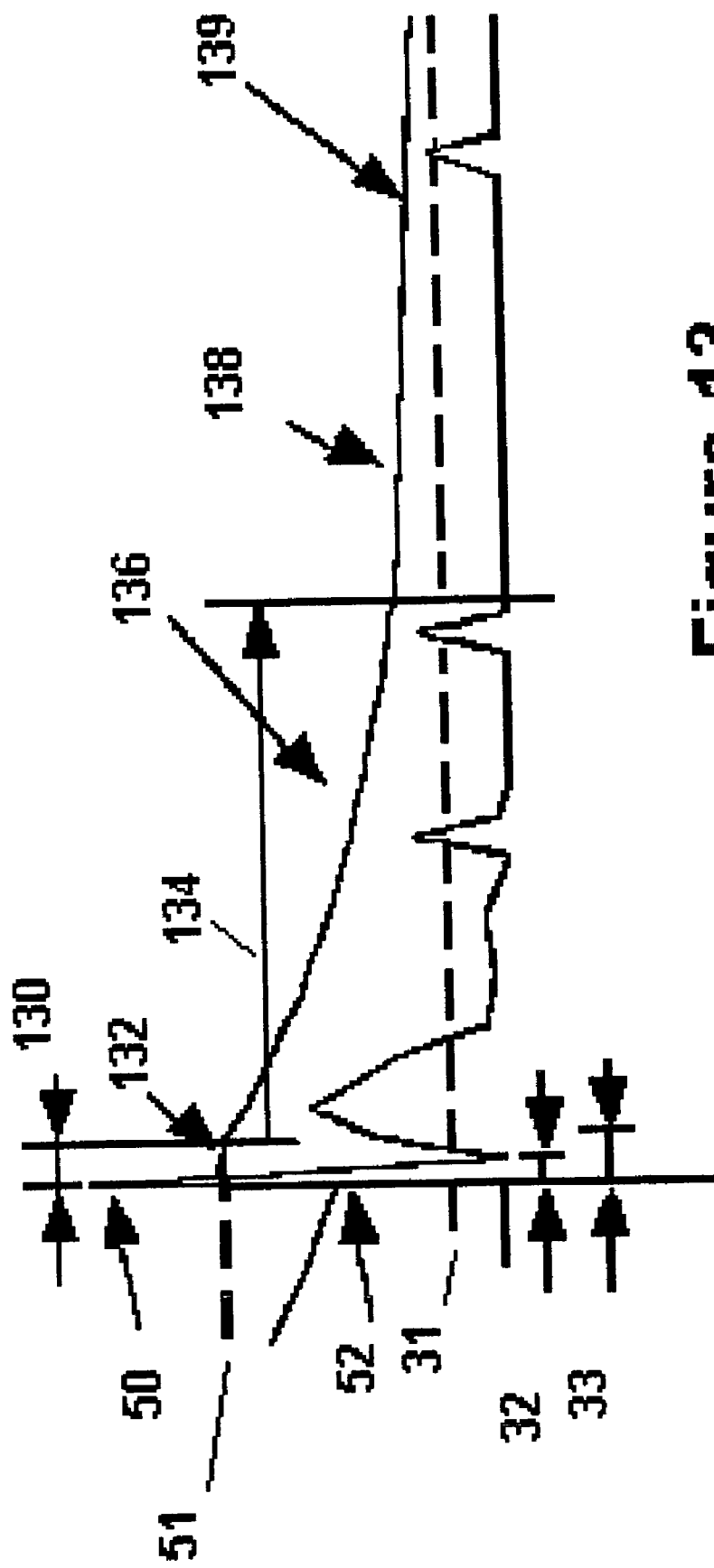
FIG. 13 is an additional embodiment of the present invention, one that uses a multi-level sensitivity threshold, starting with a relatively slow decay constant, then a relatively fast decay constant, and then a relatively slow decay time constant.

FIG. 13 discloses an additional embodiment that uses a multi-level sensitivity threshold, starting with a slow decay, then fast decay, and back to a slow decay time to avoid sensing T-waves and P-waves, as well as oversensing of noise. At the same time, it allows the ILR to sense smaller R-waves that can occur due to postural changes.

The nominal value of FL 31 is 20 ΦV (from a programmable range of 10 to 500 ΦV). The nominal value is selected to allow the ILR to continue to detect after amplitude drops of 9×. Blanking period 32, refractory period 33 and refractory extensions (not shown) also help restrict sensing to R-wave 50, while avoiding sensing of noise signals. Signals whose amplitudes are smaller than FL 31 or the auto-adjusting sensitivity threshold (AST) 139 are not sensed.

The initial level of AST 139 at 51 is set to:

$$I_0 = A_1 \text{ times } P_{max}, \text{ or } A_1 \text{ times } P_{sat} \text{ (whichever is smaller)} \quad (1)$$

$A_1$ is nominally 65% (range from 50 to 75%); $P_{max}$ is the peak amplitude of the current R-wave, and $P_{sat}$ is nominally 80% of peak amplitude (range from 70 to 90%). The starting threshold is adjusted beat-to-beat for each new $P_{max}$ unless $P_{max}$ becomes higher than the maximum value $P_{sat}$. Such large signals might be due to large amplitude muscle signals, signals from postural changes, or an abrupt, artificial loss of signal.

To avoid sensing large amplitude T-waves after an R-wave, a slow exponential decay (SED) 132 with a time constant of $S_o$ times σ is maintained during a programmable threshold hold time (THT) 130, which may be set from 0 to 500 ms, 100 ms nominally. SED is established by the following equation:

$$I = I_o \exp[-(t-t_0)/S_0 \text{ times } \sigma], \quad (2)$$

where σ is 1.3 seconds nominally (0.65 or 1.3 seconds). $S_0$ is nominally a factor of 8 (1,2,4,8,16), $t_o$ is the time at which $P_{max}$ occurs and $I_o$ is the starting threshold at time $t_0$.

After THT 130, AST 139 follows a faster exponential decay 136 during fast decay time (FDT) 134. The following equation applies:

$$I = I1 \; \text{expt}[-(t-t_1)/S_1 \text{ times } \sigma], \quad (3)$$

where $S_1$ is nominally a factor of 2 (1,2,4,8,16), $t_1$ is the time of completion of THT 130, and I1 is the threshold at $t_1$.

At the end of FDT 134 (range of 0.5 to 6.0 sec, nominally 1.5 sec), the time constant 138 is increased again by a factor to:

$$I = I2 \; \text{expt}[-(t-t_2)/S_2 \text{ times } \sigma], \quad (4)$$

where $S_2$ is nominally a factor of 8 (1,2,4,8,16), $t_2$ is the step drop time, and I2 is the threshold at $t_2$.

The blanking period 32 (50 to 120 ms, 70 ms nominally) is designed to avoid the same event and should ideally be longer than the typical filtered QRS width. Any sensed event falling within refractory period 33 (100 to 180 ms, 130 ms nominally) but after end of blanking period 32 is considered a refractory sensed event. Refractory period 33 should be set ideally to a duration longer than the widest filtered QES width. A refractory sensed event will not reset peak value 50. A refractory sensed event, however, starts a refractory extension period (50 to 150 ms, 60 ms nominally), which is not shown in this drawing for purposes of simplicity. As in previous drawings, the refractory extension(s) is designed to reject sensing of noise events and false arrhythmia events.

Figure 14:
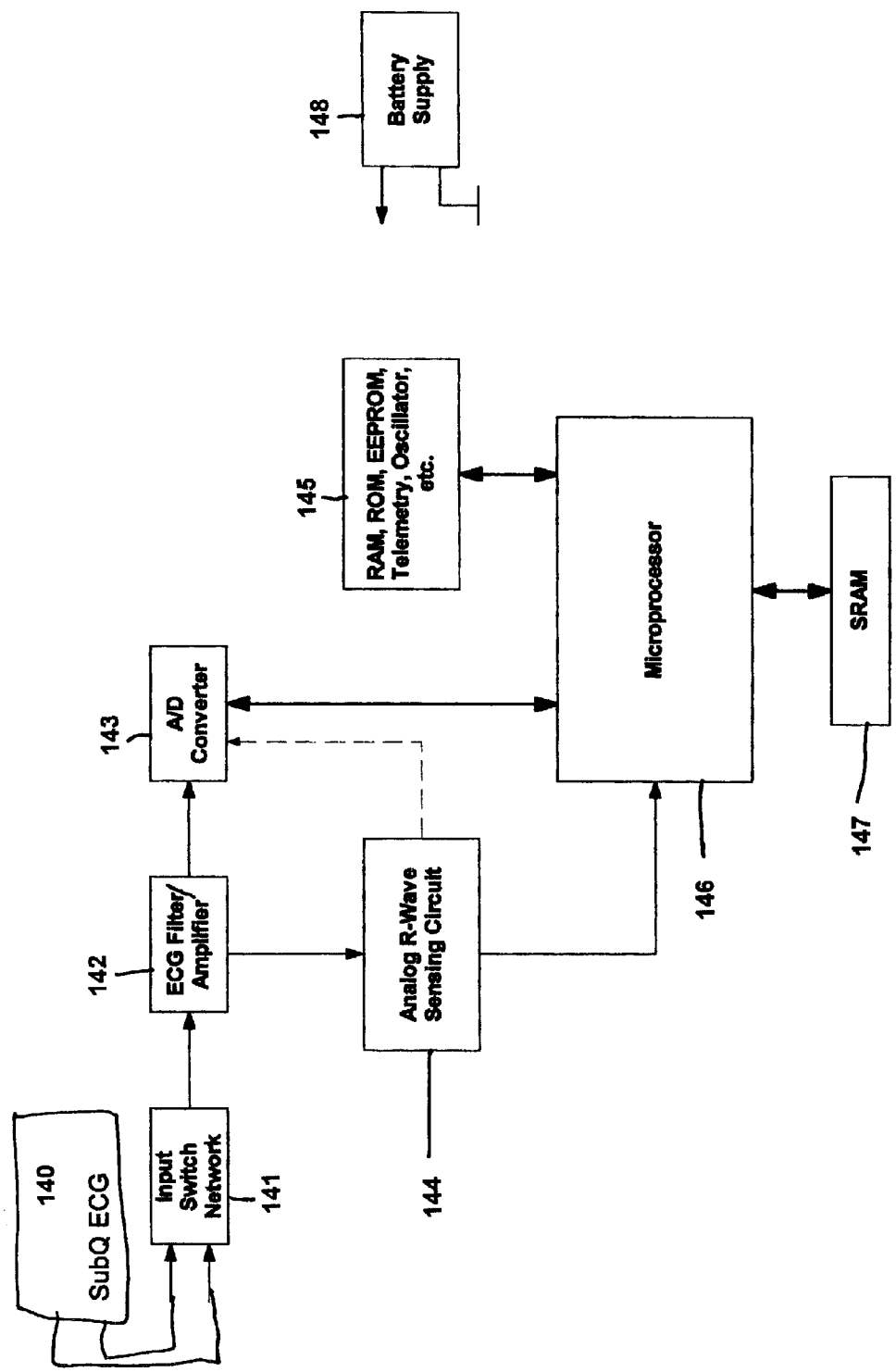
FIG. 14 is a block diagram of an analog implementation of the circuitry used in R-wave sensing in the present invention.

FIG. 14 is a block diagram of an analog circuitry implementation used for R-wave sensing in the present invention. The ILR assumes the pickup of subcutaneous (SubQ) ECG 140. The ECG signal is fed into input switch network 141. A user, usually a physician, is able to select which channel to record or sense as received from multi-channel ILRs, as implemented in the present invention. The sensing and recording channels can be different. The unfiltered signals are fed to ECG filter/amplifier 142 that has a band pass filter that can be set from 0.1 or 0.85 Hz up to 32 or 40 Hz to record signals. The signal(s) are then fed to A/D converter (ADC) 143 as well as R-wave sensing circuit 134. Preferably, a $2^{nd}$ of $3^{rd}$ order Butterworth band pass filter is used. The signal may be sent to ADC 143, if needed. R-wave sensing circuit 144 provides further filtering of the previously amplified and filtered signals. ADC 143 can record up to four channels of ECGs and one channel of activity signals. The four channels of ECGs may be two channels of unfiltered and two channels of filtered signals. The ECG and activity signals are sent directly to microprocessor 146. ADC 143 ensures that an analog signal is fed to the microprocessor. Further elements 145, 147, and 148 of the circuit and their operation are of common knowledge that those familiar with the art would be able to understand and implement an analog circuit for use in an R-wave sensing circuit.

Figure 15:
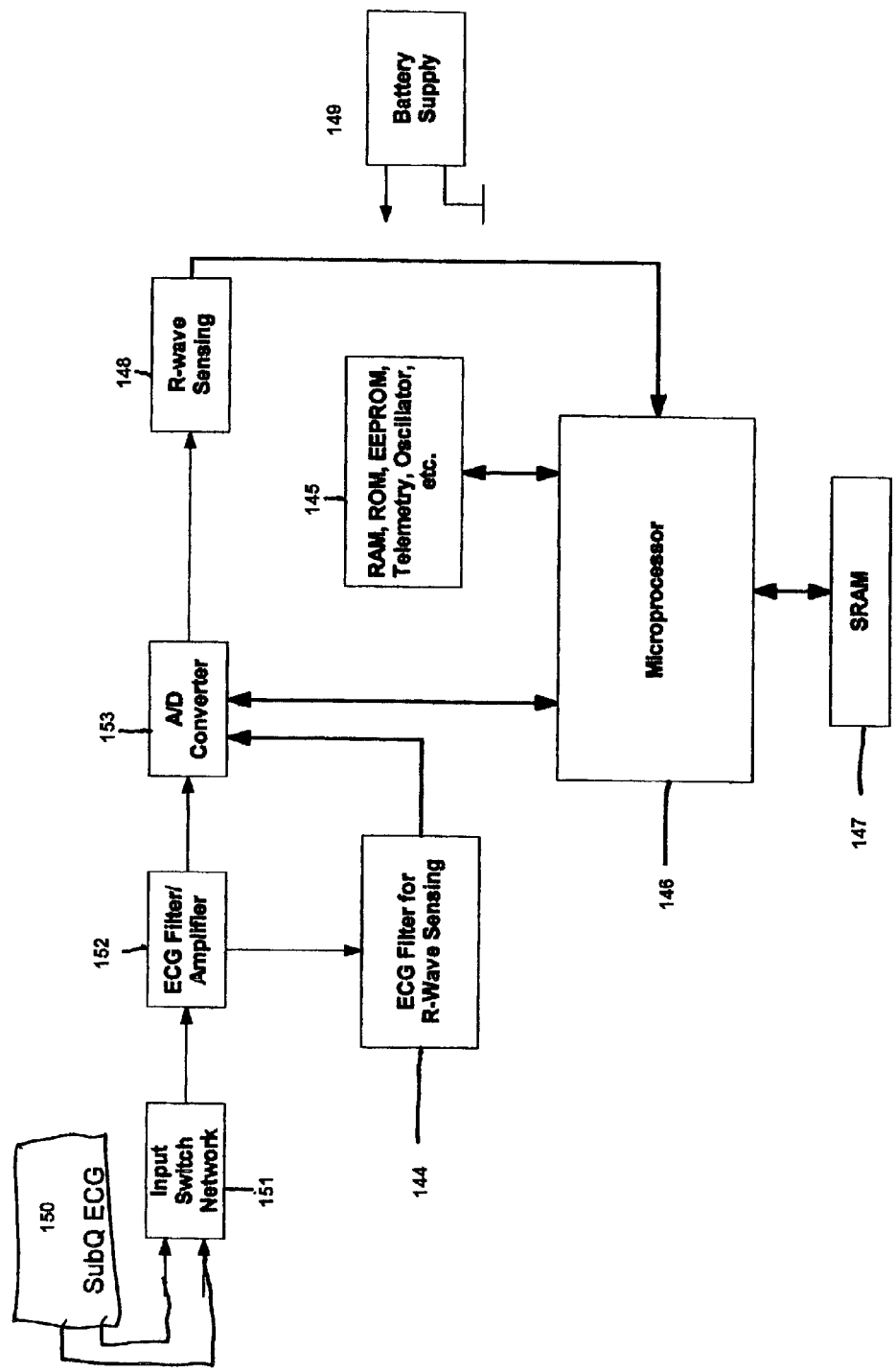
FIG. 15 is a block diagram of a digital implementation of the circuitry used in R-wave sensing in the present invention.

FIG. 15 is a block diagram of digital circuitry implementation used for R-wave sensing in the present invention. The elements of the digital circuitry are the same as those depicted in FIG. 14, except for the addition of R-wave sensing component 158. In this step, filtering occurs at a band pass of 14 to 32 Hz in ECG filter for R-wave sensing 154 and is then fed to ADC 153. The signal(s) are then converted into digital signal in ADC 153 and transferred to digital circuit component for R-wave sensing 158.

The preceding specific embodiments are illustrative of the practice of the invention. It is to be understood, therefore, that other expedients known to those of skill in the art or disclosed herein may be employed without departing from the invention or the scope of the appended claims. It is therefore to be understood that the invention may be practiced otherwise than is specifically described, without departing from the scope of the present invention. As to every element, it may be replaced by any one of infinite equivalent alternatives, only some of which are disclosed in the specification.

For example, traditional subcutaneous electrodes disposed spaced from the implantable device 10 may be used in lieu of or in addition to the electrodes coupled to the device 10. In addition, traditional transcutaneous (i.e., external) electrodes such as are routinely employed in hospitals may be used. Such electrodes are typically temporarily affixed to a patient and are generally disposable following use. In this regard, the present invention has direct application to the art of automatic external defibrillators (AEDs) and similar equipment that are used to detect (and/or provide therapy for) certain arrhythmia and asystole events, such as those supplied by Physio-Control, Inc. a division of Medtronic, Inc. Other applications for the present invention will be readily apparent to those of skill in the art following review of the present disclosure, drawings and claims and each is intended to be covered hereby and in accordance with the appended claims.

One aspect of the present invention worthy of a brief additional discussion relates to the technique for storing waveform segments. In particular, the manner for handling such segments after one or more memory locations fills. In one form of this aspect of the invention, each type of arrhythmia or each asystole receives a priority sequence tag. Thus, when a memory location fills (i.e., a new occurrence cannot be stored), the priority sequence tag is used to determine whether one or more lower priority waveforms is removed from the memory location. In addition, an entire memory "bin" may receive a priority tag so that if a higher priority bin is filled, in lieu of removing some stored items from said bin a record stored in a lower priority bin is replaced with the higher priority record (which was intended for said higher priority bin). Variations on the foregoing will be readily apparent to those of skill in the art so that the highest priority waveforms are nearly always stored for later recovery and inspection.

We claim the following:

1. A method of detecting R-waves produced by a depolarization event of a heart in an ECG waveform, comprising the steps of:

programming a minimum threshold;
   applying a first threshold for a first period of time;
   applying a second threshold for a second period of time beginning at the end of the first period of time;
   applying a third threshold for a third period of time beginning at the end of the second period of time;
   sensing ECG signals emanating from near a heart with at least one electrode; and
   recording each event as an R-wave, noise, an arrhythmia, or an asystole based on whether features of the sensed ECG waveform exceed or fail to exceed one or more of the minimum, first, second or third thresholds
   sensing a peak amplitude of an R-wave and,
   applying the peak amplitude in combination with the programmed sensitivity (PS) setting;
   calculating a threshold curve; and
   displaying the threshold curve in relation to a set of detected cardiac activity.

2. A method according to claim 1, wherein the first threshold operates according to a relatively slow decay time constant.

3. A method according to claim 2, wherein the relatively slow decay time constant has a value between about 0.5 seconds and about 10.0 seconds.

4. A method according to claim 3, wherein the second threshold has a decay time constant is shorter than the slow decay time constant of the first threshold.

5. A method according to claim 4, wherein the shorter decay time constant is between about 0.5 seconds and 5.0 seconds.

6. A method according to claim 5, wherein the third threshold has a decay time constant is shorter than the slow decay time constant of the first threshold.

7. A method according to claim 1, wherein the method is implemented in an analog electronic circuit, a digital electronic circuit, a hybrid electronic circuit, in a firmware memory location, or in an executable software routine.

8. A method according to claim 1, wherein the set of cardiac activity of the heart is essentially "real-time" cardiac activity.

9. A method according to claim 8, wherein the set of cardiac activity is filtered or rectified prior to displaying same.

10. A method according to claim 1, wherein the method is substantially completely performed by a device and said device is a one of the following: an AED, a ILR, a pacemaker, an ICD, an IPG.

11. A method according to claim 10, further comprising the steps of automatically storing a portion of the waveform after detection of an arrhythmia or an asystole.

12. A method according to claim 11, wherein the storing step occurs based on a priority sequence for each type of arrhythmia or asystole.

13. A method according to claim 12, wherein in the event that a particular higher priority bin is full, a record scheduled for storage in the particular higher priority bin instead displaces a record in a lower priority bin.

14. A method according to claim 1, wherein the at least one electrode comprises at least one of: a subcutaneous electrode, a transcutaneous electrode, an electrode coupled to a portion of the device.

15. A method according to claim 1, wherein the method is reset following occurrence of a signal saturation event.

16. An apparatus for detecting R-waves, comprising:
threshold setting means for providing at least two thresholds for a primary portion and a secondary portion of an ECG waveform, respectively;
comparing means for comparing the at least two thresholds to the primary and second portion of the ECG waveform;
logic means for determining whether each portion of the ECG waveform that exceeds a corresponding threshold is a native R-wave or is a spurious noise peak, a myopotential or other signal artifact and whether an arrhythmia or an asystole has occurred; and
storage means for storing portions of the ECG waveform for which an arrhythmia or an asystole is determined to have occurred wherein the storage means operates according to a priority sequence so that in the event that a limited storage event occurs, a lower priority ECG waveform is displaced by a higher priority ECG waveform.

17. An apparatus according to claim 16, wherein the apparatus is reset following occurrence of a signal saturation event.

* * * * *

UNITED STATES PATENT AND TRADEMARK OFFICE
CERTIFICATE OF CORRECTION

| | | |
|---|---|---|
| PATENT NO. | : 7,027,858 B2 | Page 1 of 1 |
| APPLICATION NO. | : 10/238140 | |
| DATED | : April 11, 2006 | |
| INVENTOR(S) | : Jian Cao et al. | |

It is certified that error appears in the above-identified patent and that said Letters Patent is hereby corrected as shown below:

On the title page item (75) Inventors: delete "Lee B. Brian" and insert --Brian B. Lee--.

Signed and Sealed this

Second Day of January, 2007

JON W. DUDAS
*Director of the United States Patent and Trademark Office*